(12) United States Patent
Takalo et al.

(10) Patent No.: US 11,614,445 B2
(45) Date of Patent: Mar. 28, 2023

(54) BACKGROUND BLOCKERS FOR BINDING ASSAYS

(71) Applicant: Radiometer Turku Oy, Turku (FI)

(72) Inventors: Harri Takalo, Turku (FI); Kaj Blomberg, Turku (FI); Henri Sund, Turku (FI)

(73) Assignee: RADIOMETER TURKU OY, Turku (FI)

( * ) Notice: Subject to any disclaimer, the term of this patent is extended or adjusted under 35 U.S.C. 154(b) by 597 days.

(21) Appl. No.: 16/306,997

(22) PCT Filed: Jun. 6, 2017

(86) PCT No.: PCT/EP2017/063676
§ 371 (c)(1),
(2) Date: Dec. 4, 2018

(87) PCT Pub. No.: WO2017/211799
PCT Pub. Date: Dec. 14, 2017

(65) Prior Publication Data
US 2021/0140970 A1 May 13, 2021

(30) Foreign Application Priority Data

Jun. 9, 2016 (DK) .......................... PA 2016 00339

(51) Int. Cl.
| | |
|---|---|
| *G01N 33/58* | (2006.01) |
| *C09K 11/07* | (2006.01) |
| *G01N 33/53* | (2006.01) |
| *G01N 21/64* | (2006.01) |
| *G01N 33/543* | (2006.01) |

(52) U.S. Cl.
CPC .......... *G01N 33/5306* (2013.01); *C09K 11/07* (2013.01); *G01N 21/6408* (2013.01); *G01N 33/543* (2013.01); *G01N 33/582* (2013.01); *C09K 2211/182* (2013.01); *C12Q 2565/518* (2013.01); *G01N 2458/40* (2013.01)

(58) Field of Classification Search
CPC ... C09K 11/06; C09K 11/07; C09K 2211/182; C12Q 2565/518; G01N 21/6408; G01N 2458/40; G01N 33/5306; G01N 33/543; G01N 33/582
See application file for complete search history.

(56) References Cited

U.S. PATENT DOCUMENTS

| | | | |
|---|---|---|---|
| 2013/0183771 A1 | 7/2013 | Meltola et al. | |
| 2013/0210165 A1* | 8/2013 | Meltola .............. | G01N 21/6486 436/501 |
| 2014/0336373 A1* | 11/2014 | Lamarque ............ | C07D 255/02 540/474 |

FOREIGN PATENT DOCUMENTS

| | | |
|---|---|---|
| CN | 101027559 A | 8/2007 |
| CN | 103890137 A | 6/2014 |
| CN | 104125997 A | 10/2014 |
| EP | 0 617 286 A2 | 9/1994 |
| EP | 1 150 985 B1 | 6/2004 |
| JP | 62-18868 | 1/1987 |
| JP | 6-317593 | 11/1994 |
| JP | 2802921 | 7/1998 |
| JP | 2014-529599 | 11/2014 |
| WO | WO 87/07955 | 12/1987 |
| WO | WO 03/012127 A2 | 2/2003 |
| WO | WO 2013/026790 A1 | 2/2013 |
| WO | WO 2013/092992 A1 | 6/2013 |
| WO | WO 2016/006641 A1 | 1/2016 |
| WO | WO 2016/066641 A1 * | 5/2016 |

OTHER PUBLICATIONS

Bookout et al., "Development of a Dual-Label Time-Resolved Fluorometric Immunoassay for the Simultaneous Detection of Two Recombinant Proteins in Potato," J. Agric. Food Chem., 2000, vol. 48, No. 12, pp. 5868-5873.*

Huang et al., "Application of time-resolved fluorescence immunoassay for detection of alpha-fetoprotein and the clinical significance thereof," Fujian Med. J., 2006, vol. 28. No. 1, pp. 115-116; and English translation, 4 pages.*

Hagan, A.K. et al., "Lanthanide-based time-resolved luminescence immunoassays," Analytical and Bioanalytical Chemistry, vol. 400, No. 9, pp. 2847-2864 (2011).

Myyryläinen, Tiina, et al., "Simultaneous detection of Human Immunodeficiency Virus 1 and Hepatitis B virus infections using a dual-label time-resolved fluorometic assay," Journal of Nanobiotechnology, vol. 8, No. 1, p. 27 (2010) (six pages).

Valenzano, Kenneth J., et al., "Development of a Fluorescent Ligand-Binding Assay Using the AcroWell Filter Plate," Journal of Biomolecular Screening, vol. 5, No. 6, pp. 455-461 (2000).

International Search Report of International Application No. PCT/EP2017/063676, dated Aug. 14, 2017 (three pages).

Written Opinion of the International Searching Authority for International Application No. PCT/EP2017/063676 (six pages), dated Aug. 14, 2017.

Blomberg, Kaj et al., "Fluorescent europium chelates as target cell markers in the assessment of natural killer cell cytotoxicity," *Journal of Immunological Methods*, vol. 160, pp. 27-34 (1993).

Hagren, Virve et al., "An automated PCR platform with homogeneous time-resolved fluorescence detection and dry chemistry assay kits," *Analytical Biochemistry*, vol. 374, pp. 411-416 (2008).

\* cited by examiner

*Primary Examiner* — Galina M. Yakovleva

(74) *Attorney, Agent, or Firm* — Finnegan, Henderson, Farabow, Garrett & Dunner, LLP

(57) ABSTRACT

The present invention relates to a background blocking concept for use in time-resolved fluorometry binding assays. More particular, the invention relates to a binding assay and a kit involving the use of the same or similar chelating ligand in lanthanide chelate-labelled analyte-specific biomolecules and as or in a background blocking agent.

2 Claims, 9 Drawing Sheets

Scheme 1

Scheme 2

Scheme 3

Scheme 5

Scheme 6

Scheme 7

21

20

Scheme 8

BACKGROUND BLOCKERS FOR BINDING ASSAYS

Figure 1:
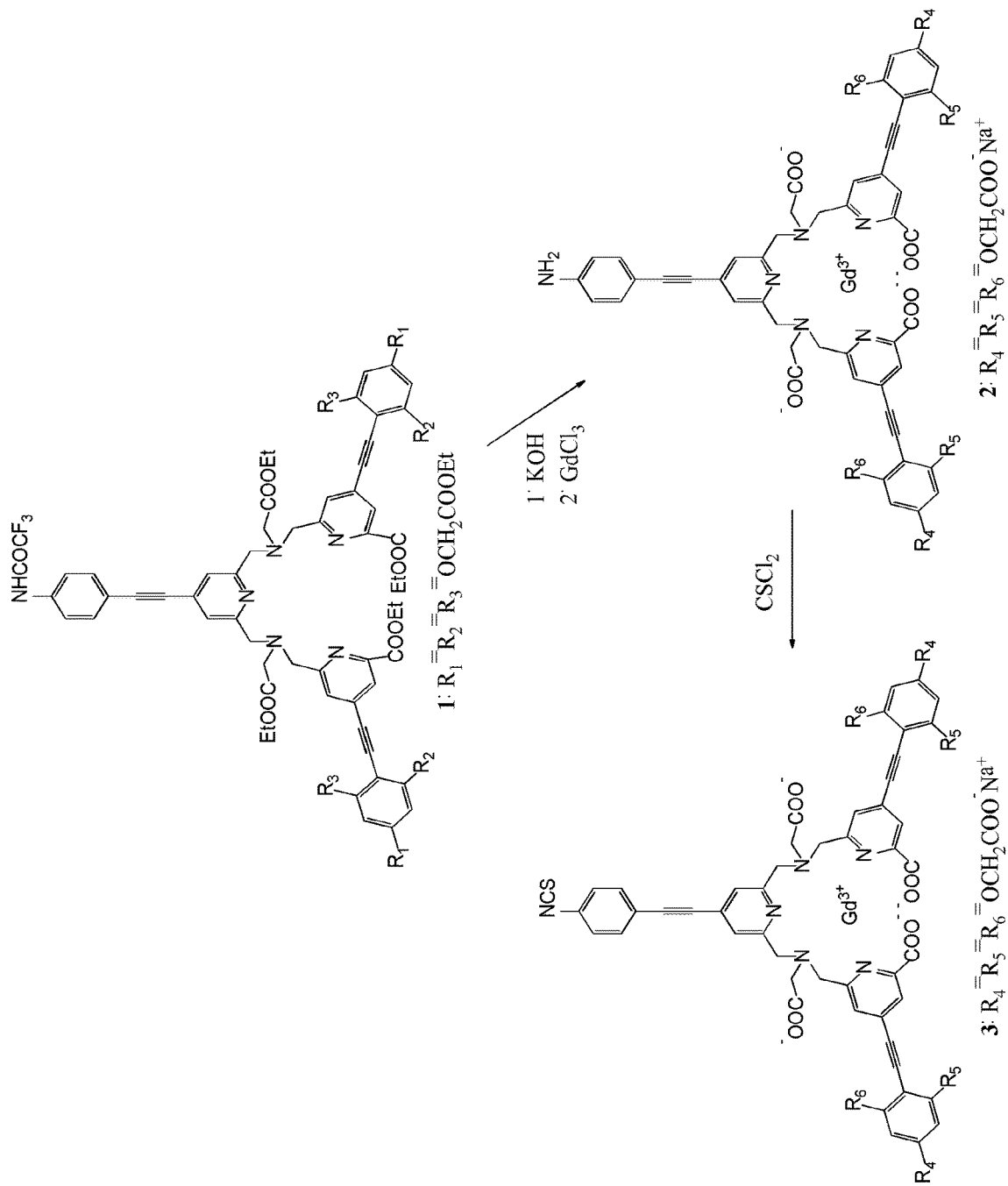

This application is a national stage filing under 35 U.S.C. § 371 of International Application No. PCT/EP2017/063676, filed on Jun. 6, 2017, which claims priority of Danish Patent Application No. PA 2016 00339, filed on Jun. 9, 2016. The contents of these applications are each incorporated herein by reference.

FIELD OF THE INVENTION

The present invention relates to a background blocking concept in time-resolved fluorometry binding assays. More particular, the invention relates to binding assays, in particular bio-affinity assays, involving lanthanide chelates which take advantage of the blocking of non-specific background luminescence in time-resolved fluorometry, the use of such non-specific blockers and a kit for use in binding assays.

BACKGROUND OF INVENTION

Time-resolved fluorometry (TRF), employing long-lifetime emitting luminescent lanthanide chelates, has been applied in many specific binding assays, such as e.g. immunoassays, DNA hybridization assays, receptor-binding assays, enzymatic assays, ligand binding assays, bio-imaging such as immunocytochemical and immunohistochemical assays, and cell based assays to measure interesting analytes at very low concentrations.

A well-known challenge when designing chelates and ligands possessing multiple hydrophobic aromatic chromophores is to obtain a molecular structure which offers high water solubility, and at the same time, is inert towards any possible bioprocesses and other substances present in the target assay. Good water solubility is essential when fluorescent chelates are used for biomolecule labeling, genetically engineered molecules, and semisynthetic or synthetic molecules.

Lately, improved luminescence intensities have been demonstrated with lanthanide chelates which have three independent chromophoric moieties, such as a substituted 4-phenylethynylpyridine combined in various chelate or ligand structure designs.

WO 2013/026790 discloses a luminescent lanthanide chelate with lanthanides such as europium, as well as the corresponding luminescence lanthanide chelating ligand. The application further discloses a detectable molecule comprising a bio-specific binding reactant (such as an antibody) conjugated to the luminescent lanthanide chelate, as well as a method of carrying out a bio-specific binding assay, the use of such a detectable molecule in a specific bio-affinity based binding assay utilizing time-resolved fluorometric determination of a specific luminescence, and a solid support material conjugated with the luminescent lanthanide chelate.

WO 2013/092992 discloses luminescent lanthanide chelates having three 4-(phenylethynyl)pyridine chromophoric groups tethered to an acyclic core. In some embodiments, one chromophoric group comprises a reactive group and the other two chromophoric groups comprise two or three —$OCH_2CO_2H$ groups in the ortho and/or para positions.

WO 2013/011236 discloses luminescent lanthanide chelates having three 4-(phenylethynyl)pyridine chromophoric groups tethered to a triazamacrocyclic core. The 4-(phenylethynyl)pyridine chromophoric groups are substituted at the para-position of the phenyl ring with an electron donating group.

WO 2014/147288 discloses triazacyclononane-based lanthanide chelate complexes useful as labelling reagents. The disclosed chelates have three 4-(phenylethynyl)pyridine chromophoric groups, one of which chromophoric groups comprises a reactive group; the other two chromophoric groups have either (i) two carboxyl (—$CO_2H$) substituents on the phenyl ring in the meta and para positions, or (ii) two —$OCH_2CO_2H$ groups on the phenyl ring in the meta positions.

WO 2014/162105 relates to luminescent lanthanide complexes having a chelating agent formed by three ligands incorporating a 2,6-pyridine-di-carboxylic group or formed by a macrocycle having a 1,4,7-triazacyclononane structure.

WO 2016/066641 relates to an azamacrocyclic lanthanide chelate design having substituted 4-(phenylethynyl)pyridine chromophores around an emitting lanthanide core. The chromophores have high molar absorptivity and luminescence with lanthanide ions. The application further discloses the ligand from which the chelate is prepared, and chelates attached to a bio-specific reactant and their use in various assays.

It is known that the addition of chromophores decreases the solubility of ligands and chelates in water, increases the formation of bio-specific binding reactant aggregates during the labeling process and increases the non-specific binding properties of labeled molecules. Aggregates will create purification problems and reduced yield of labeled material. Moreover, increased non-specific binding of labeled molecules will enhance background luminescence of bio-specific assays, and thus, reduce assay sensitivity. At the same time, when the specific signal intensity in the assay is enhanced, a reduction of background signal and other interfering factors is a difficult task to achieve. Additional interfering factors include the sample matrix and other components in the assay, which can each have a negative effect on the performance of the assay (Hemmila I., Photoluminescence immunoassays. In: Johnstone, A. P., Turner, M. W., eds., Immunochemistry 1: a practical approach. IRL Press Oxford, 1997, 193-214).

In immunoassays unwanted non-specific binding is caused by an interaction between 1) the reporter antibody and proteins, 2) the reporter antibody and the solid phase, 3) dry reagents used for stabilizing and storing biomolecules before the actual assay, and 4) the reporter antibody and compounds of the sample matrix and other reagents used in the assay. The attraction forces leading to the non-specific binding are ion-ion interactions, hydrogen bonding and Van der Waals attraction forces (i.e. attraction caused by two molecules having permanent opposite dipoles, dipolar molecules induce dipoles in other molecules and attractive forces between non-polar molecules).

The non-specific binding is normally minimized by blocking remaining binding sites (Jianwen, He., Practical Guide to ELISA development. In: Wild, D. ed., The Immunoassay Handbook, Theory and applications of ligand binding, ELISA and related techniques. Elsevier Oxford, 2013, 381-394). Proteins and surfactants (detergents) are the two main classes of blocking agents (Steinitz, M., Quantification of the blocking effect of Tween 20 and bovine serum albumin in ELISA microwells. Anal. Biochem. 2000, 282: 232-238). The commonly used blocking proteins include e.g. bovine serum albumin, casein, non-fat dry milk, fish gelatin and whole sera (Vogt, R. F., Philips, D. L. et al., Quantitative differences among various proteins as blocking agents for ELISA microtiter plates. J. Immunol. Methods 1987, 101:43-50). The surfactants can be non-ionic (such as Tween 20), anionic (such as sodium dodecyl-benzene-sulfonate), cationic (such as hexadecyltrimethylammonium bromide) and zwitter-ionic (such as CHAPS hydrate).

Also polymeric blockers (such as polyvinyl alcohol, polyvinylpyrrolidone, polyacrylic acid, polyacrylic maleic acid and polyethylene glycol) and inorganic ions (such as $SO_4^{2-}$, $HPO_4^{2-}$, $Mg^{2+}$, $Ca^{2+}$, $Li^+$, $Na^+$, $H^+$, $OH^-$ and $PO_4^{3-}$) are well-known blocking agents (WO 2012/161288, Immunoassay methods and reagents for decreasing non-specific binding).

There is a desire in the art to develop new improved blocking reagents for the reduction of the non-specific binding phenomenon such as the background and other interfering factors in TRF binding assays, such as bio-affinity assays using lanthanide labeled reporters.

SUMMARY OF THE INVENTION

The aim of the present invention is to provide improved background blocking reagents to be used in analyte-specific binding assays and especially in bio-affinity binding assays, such as immunoassays (both homogeneous and heterogeneous), nucleic acid hybridization assays, receptor-binding assays, enzymatic assays, ligand binding assays, immunocytochemical assays, immunohistochemical assays and cell based assays utilizing fluorometric or time-resolved fluorometric (TRF) determination of specific luminescence. Improved assay sensitivity can be obtained by using the blockers of the present invention.

In particular, the present invention provides background blocking reagents which prevent non-specific binding of the fluorescent labelled analyte-specific components on the surface of solid support used for the assay.

The aim is to have highly stable and water soluble, preferably non-fluorescent chelates containing several chromophore moieties (1-5 moieties), which can (if desired) be covalently conjugated to non-specific biomolecules, to increase the tendency of the non-specific binding on the surface used in the assay in question. At the same time, the biomolecules, when conjugated with the blocking reagents, should not increase binding towards the actual labeled molecules or analytes used in the assay.

It has now surprisingly been found that in TRF binding assays, utilizing chelated fluorescent lanthanide ions (e.g. $Eu^{3+}$) for labeling of specific biomolecules (e.g. antibodies), the non-specific background luminescence could be reduced significantly by using a blocking reagent sharing the same or similar chromophoric chelating ligand structure as that of the labelling fluorescent lanthanide chelate, with the exception that the blocking reagent has a different, or no lanthanide coordination ion. For example, in a TRF binding assays where an analyte-specific biomolecule is labelled with a fluorescent $Eu^{3+}$ ion chelate, a suitable blocking reagent may be based on the same or similar form of the chelating ligand, but wherein the fluorescent coordination lanthanide ion $Eu^{3+}$ is substituted by the non-fluorescent lanthanide ion $Gd^{3+}$ in the chelating ligand. More surprising is that with a fluorescent acyclic lanthanide chelate, a blocking reagent with similar chromophoric moiety or moieties but having at least one cyclic chelating moiety with or without a chelating ion and optionally conjugated to a non-specific biomolecule could be used to reduce background. Alternatively, a lanthanide ion with a different emission wavelength than the lanthanide ion used to label the specific biomolecule could be used. In another alternative, the chelating ligand without a lanthanide coordination ion could be used as the blocking reagent. A combination of different chelated lanthanide ions (or no ion) could also be used, for example for use as internal controls. Different analytes could be detected in the same assay applying the present blocking reagent by labelling different analyte-specific binding components with similar or identical lanthanide chelates, wherein each different analyte-specific binding component is labelled with its own individual lanthanide ion, wherein the different lanthanide ions can be detected separately from the other ions. The blocking reagent should have high non-specific binding properties to prevent non-specific binding of the labeled specific biomolecule. A way of enhancing the non-specific binding properties of the blocking agent is to link a non-specific biomolecule, e.g. non-specific protein, nonsense IgG, similar biomolecules to the chelating ligand, to link a hapten such as biotin, to an organic molecule (hydrophobic group) or to link a polymer.

So far no-one has disclosed the idea of using compounds and/or conjugates that are similar in structure to the lanthanide label bound to the analyte-specific component, e.g. a biomolecule, to reduce the non-specific binding phenomenon such as the background and other interfering factors in binding assays, such as bio-affinity based binding assays.

As a whole, the background blocking principle of the present invention can be effectively applied by using individual chelates and ligands, chelates and ligands conjugated to suitable binding components, in particular biomolecules such as antibodies, ligands conjugated to a polymer, ligands conjugated to an organic molecule and ligands conjugated to a hapten such as biotin, and thus, ligands immobilized to a streptavidin coated surface, or surface coated with a detection bio-specific molecule or other proteins.

In a first aspect, the present invention concerns a binding assay for detecting one or more specific analyte(s) in a sample comprising:
  providing a first analyte-specific binding component or a set of different first analyte-specific binding components being specific to different analytes, immobilized onto a coated or uncoated solid support,
  adding: 1) a second analyte-specific binding component labelled with a luminescent lanthanide chelate or a set of different second analyte-specific binding components specific to said different analytes labelled with luminescent lanthanide chelates comprising different lanthanide ions; 2) a non-specific reagent comprising or being a lanthanide chelate or chelating ligand, which reagent is non-specific to the said analyte(s) and to said first and second analyte-specific binding components; and 3) said sample; and
  detecting the specific analyte(s) by time-resolved fluorometry (TRF).

The non-specific reagent may be added before, at the same time as or after said labelled analyte-specific binding component(s) has been added. Depending on the assay this could be performed by adding the labelled analyte-specific binding component(s) in, e.g., the incubation buffer, the sample, or washing fluid.

In a second aspect, the present invention concerns a kit for use in detecting one or more specific analyte(s) in a sample in a binding assay, said kit comprising: 1) a first analyte-specific binding component or a set of different first analyte-specific binding components being specific to different analytes, immobilized onto a coated or uncoated solid support; 2) a second analyte-specific binding component labelled with a lanthanide chelate or a set of different second analyte-specific binding components specific to said different analytes labelled with luminescent lanthanide chelates comprising different lanthanide ions, and 3) a non-specific reagent, which is non-specific to the said analyte(s) and to said first and second analyte-specific binding components, and is or comprises a lanthanide chelate or a chelating ligand.

In a preferred embodiment, at least one of said first and second analyte-specific binding components is a biomolecule. More preferred, both the first and second analyte-specific binding components are biomolecules The first analyte-specific binding component or set of different analyte-specific binding components is/are immobilized directly on the coated or uncoated solid support or on the coated or uncoated solid support via a pair of binding ligands.

In a preferred embodiment of the first and second aspect, the binding assay and the kit are for detecting one specific analyte in a sample, and comprise a first analyte-specific binding component immobilized onto a coated or uncoated solid support, a second analyte-specific binding component labelled with a luminescent lanthanide chelate, and said non-specific reagent.

In a third aspect, the present invention concerns the use of a background blocking reagent in a binding assay for detecting one or more specific analyte(s) in a sample by time-resolved fluorometry (TRF), comprising a first analyte-specific binding component or set of different first analyte-specific binding components immobilized on a coated or uncoated solid support, and a second analyte-specific binding component labelled with a lanthanide chelate or a set of different second analyte-specific binding components specific to said different analytes labelled with luminescent lanthanide chelates comprising different lanthanide ions, wherein the background blocking reagent is a non-specific reagent, which is non-specific to the said analyte(s) and to said first and second analyte-specific binding components, and is or comprises a lanthanide chelate or a chelating ligand.

In a preferred embodiment, the chelating ligand being or comprised in the non-specific reagent is similar to the chelating ligand comprised in the luminescent lanthanide chelate(s) used to label the analyte(s). The luminescent lanthanide chelates used to label different analytes comprise different lanthanides, and may be the same or different chelating ligands. In another preferred embodiment, the chelating ligand being or comprised in the non-specific reagent is identical to the chelating ligand comprised in the luminescent lanthanide chelate(s) used to label the analyte(s).

In all aspects of the present invention, the non-specific reagent is selected from:
i) a biomolecule labelled with a lanthanide chelate, wherein said biomolecule is non-specific to said analyte(s) and to said first and second analyte-specific binding components, and the lanthanide ion is different from the lanthanide ion(s) in the said lanthanide chelate labelled specific binding component(s),
ii) a biomolecule labelled with a chelating ligand, wherein said biomolecule is non-specific to said analyte(s) and to said first and second analyte-specific binding components, and no lanthanide ion is present,
iii) a lanthanide chelate comprising no biomolecule, wherein the lanthanide ion is different from the lanthanide ion(s) in said lanthanide chelate labelled specific binding component(s), or
iv) a chelating ligand comprising no biomolecule and no lanthanide ion.

In one embodiment, the second analyte-specific binding component is replaced by an analyte labelled with a luminescent lanthanide chelate or a set of different labelled analytes, each analyte being labelled with a different luminescent lanthanide chelate comprising a different lanthanide ion, and wherein the non-specific reagent is selected from:
v) analyte analogue(s) labelled with a second lanthanide chelate, wherein said analyte analogue(s) is/are not recognized by the first analyte-specific binding component(s), and the lanthanide ion(s) is/are different from the lanthanide ion(s) in said luminescent lanthanide chelate labelled analyte,
vi) a chelating ligand labelled analyte analogue(s), wherein the analyte analogue(s) is/are not recognized by the first analyte-specific binding component(s), and no lanthanide ion is present,
vii) a second lanthanide chelate comprising no analyte analogue and the lanthanide ion(s) is/are different from the lanthanide ion(s) in said lanthanide chelate labelled analyte(s), or
viii) a chelating ligand comprising no analyte analogue(s) and no lanthanide ion(s).

In another embodiment, the biomolecule used in a non-specific reagent is dissimilar to the analyte or analytes to be detected or even completely un-related. In another embodiment, the biomolecule is an analyte analogue, e.g. a derivative, a fusion, a mutant, or the like. However, it is a requirement that a biomolecule to be useful in a non-specific reagent is not recognized by the first and the second analyte-specific binding components or the analyte labelled with a luminescent lanthanide chelate when the second analyte-specific binding components is replaced.

In a preferred embodiment of the invention, the chelating ligand used as, or in, the non-specific reagent has the same or similar structure as the chelating ligand used to label the second analyte-specific binding component(s); and even more preferred, the chelating ligand used in, or as, the non-specific reagent is the same as the chelating ligand used to label the said second analyte-specific binding component(s). The second analyte-specific binding component is either absent or is replaced by a non-specific binding component, in particular a biomolecule, such as a nonsense antibody or other protein, in the non-specific reagent. The chelated lanthanide ion in the non-specific reagent is different from the lanthanide ion used to label the second analyte-specific binding component(s). The chelating ligand may also be used as, or in, the non-specific reagent without any coordination ion. In a most preferred embodiment, the non-specific reagent is not conjugated to a biomolecule and is without any coordination ion. Moreover, the non-specific reagent preferably has at least one cyclic chelating moiety.

DRAWINGS

Figure 2:
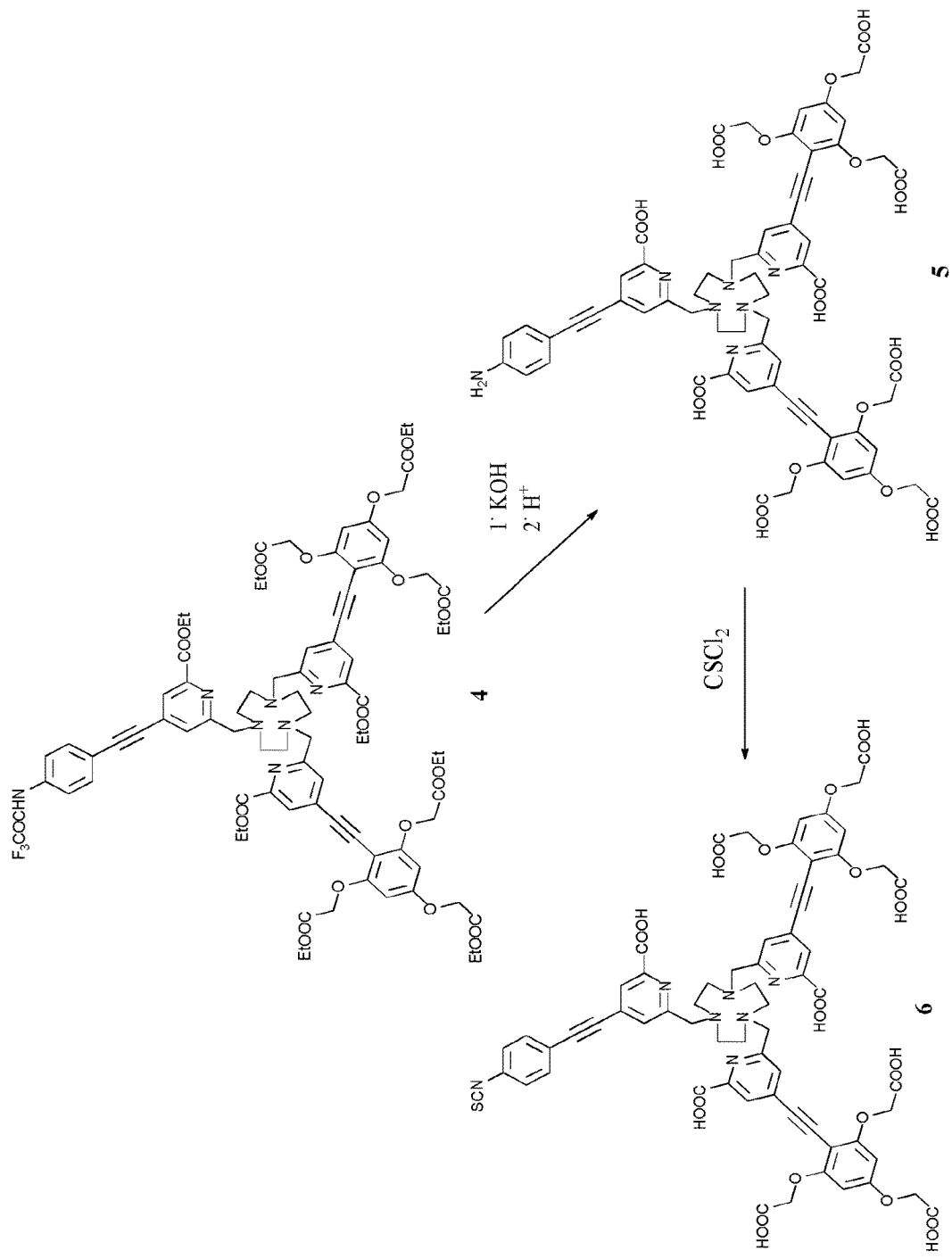
Figure 3:
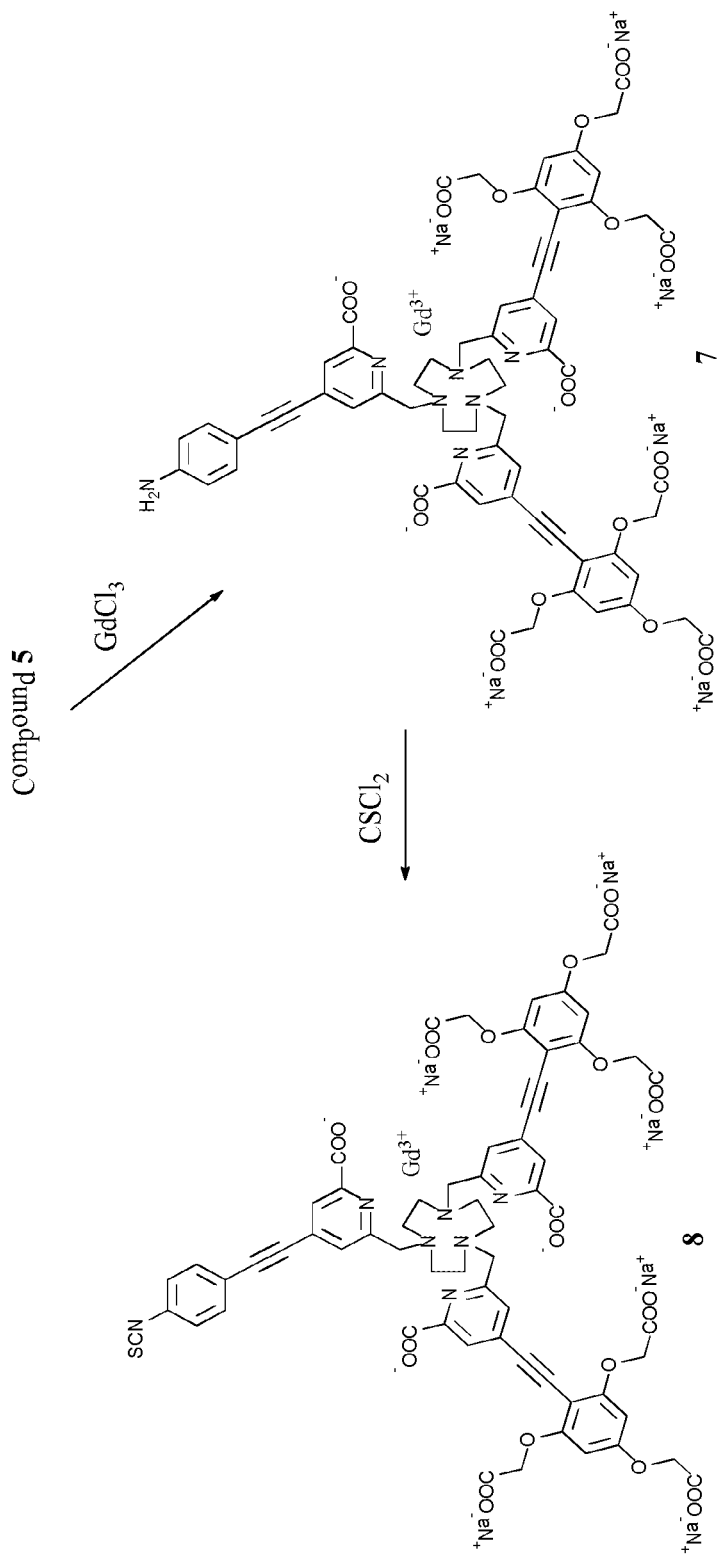
Figure 4:
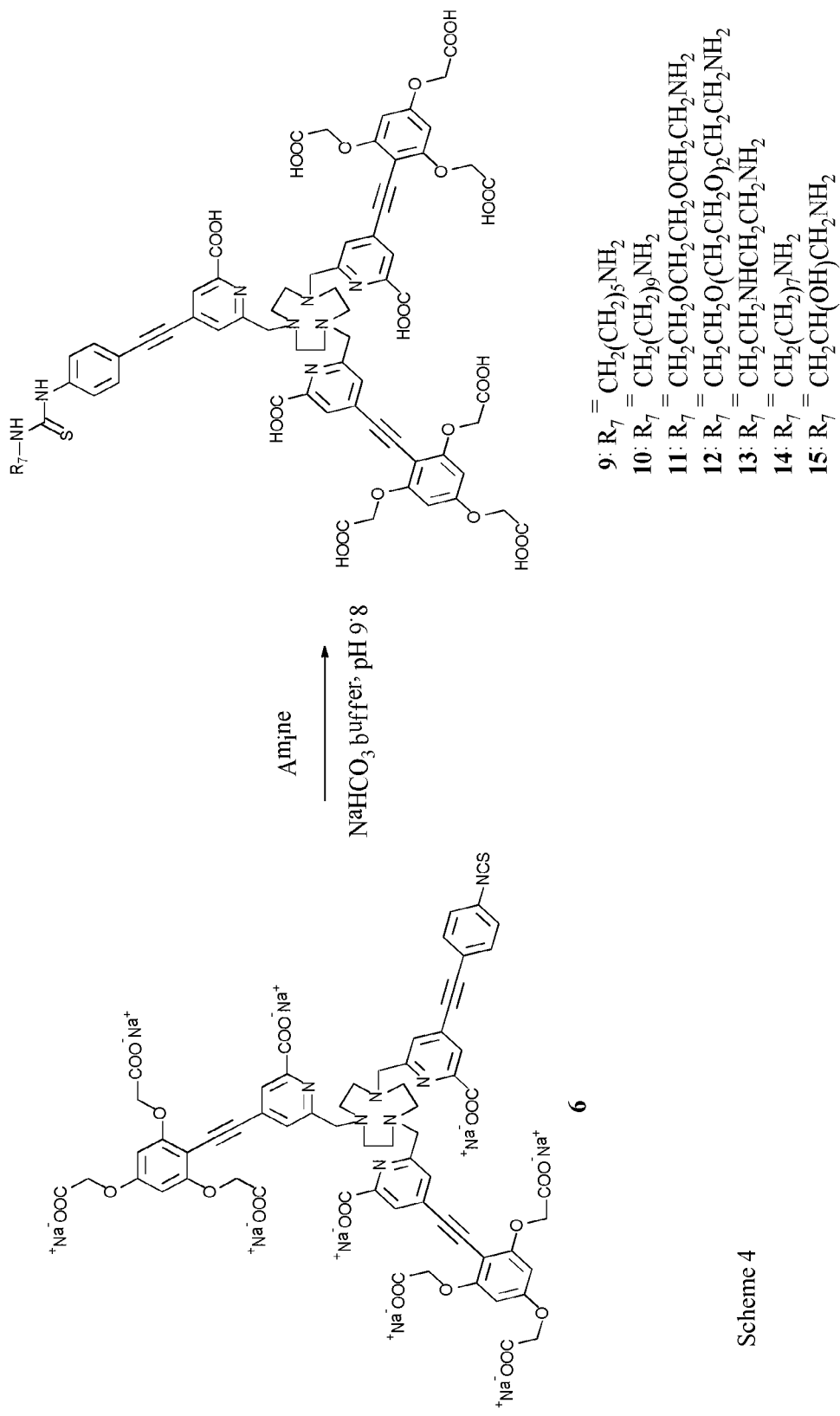
Figure 5:
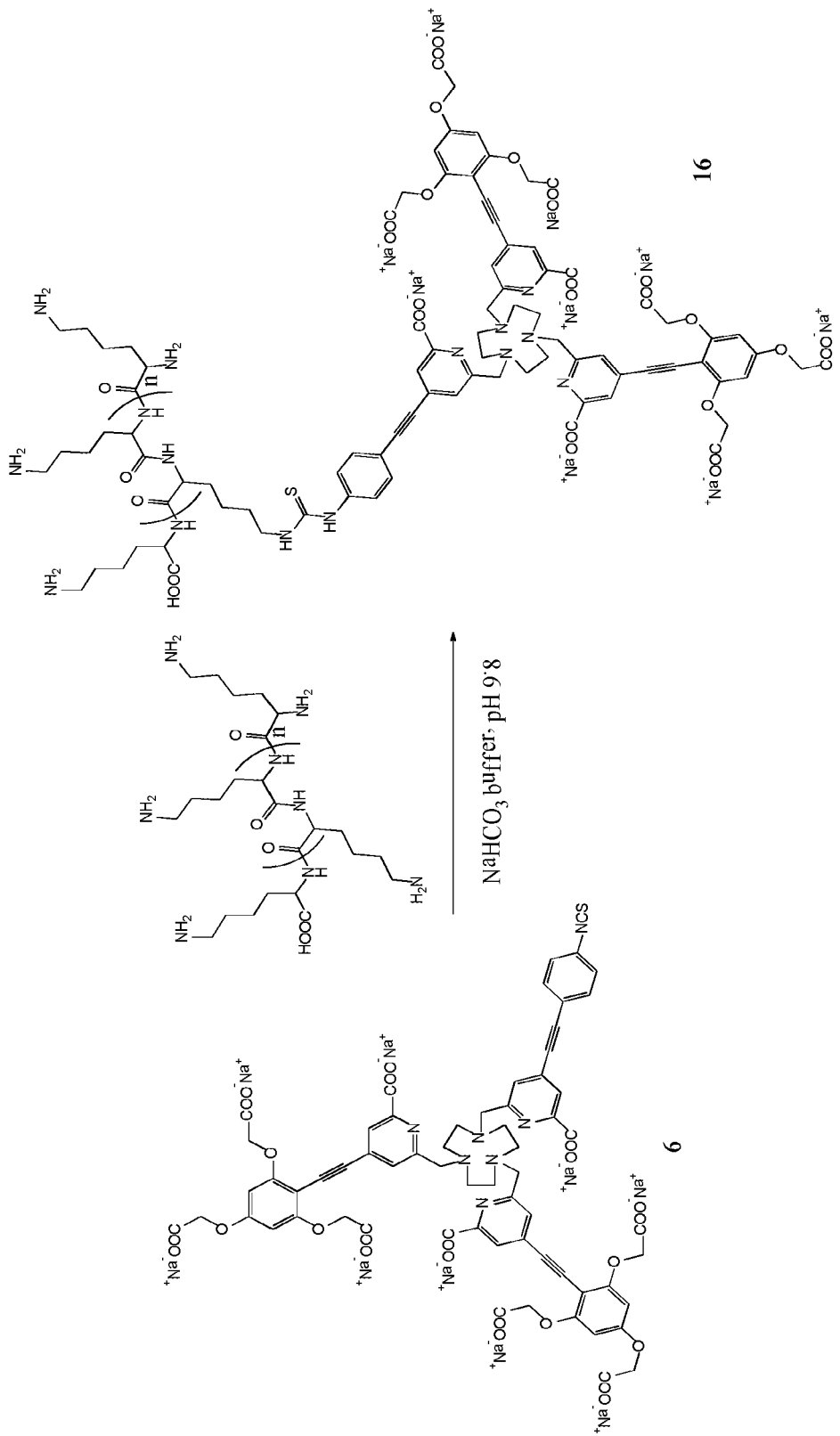
Figure 6:
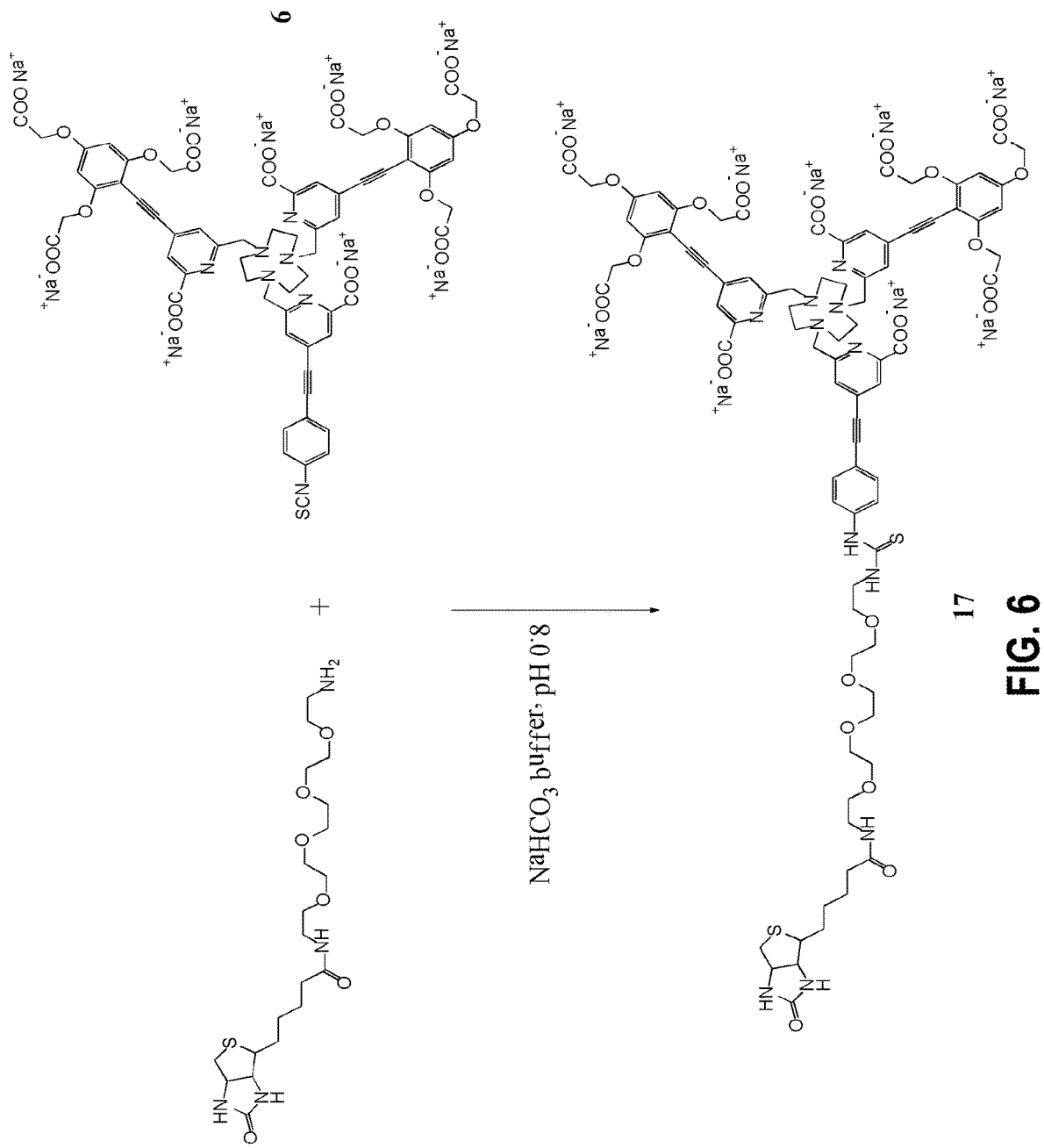
Figure 7:
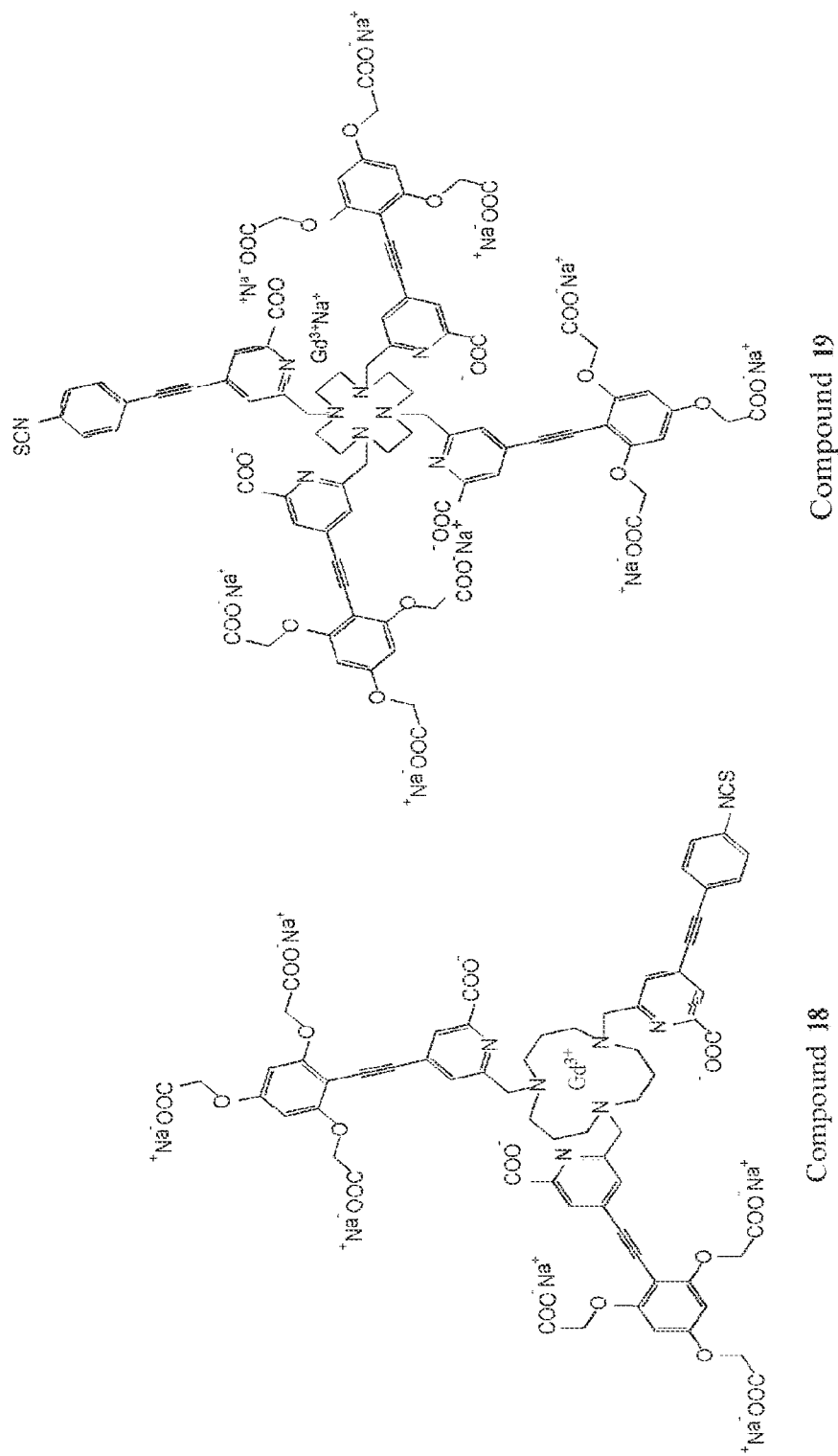
Figure 8:
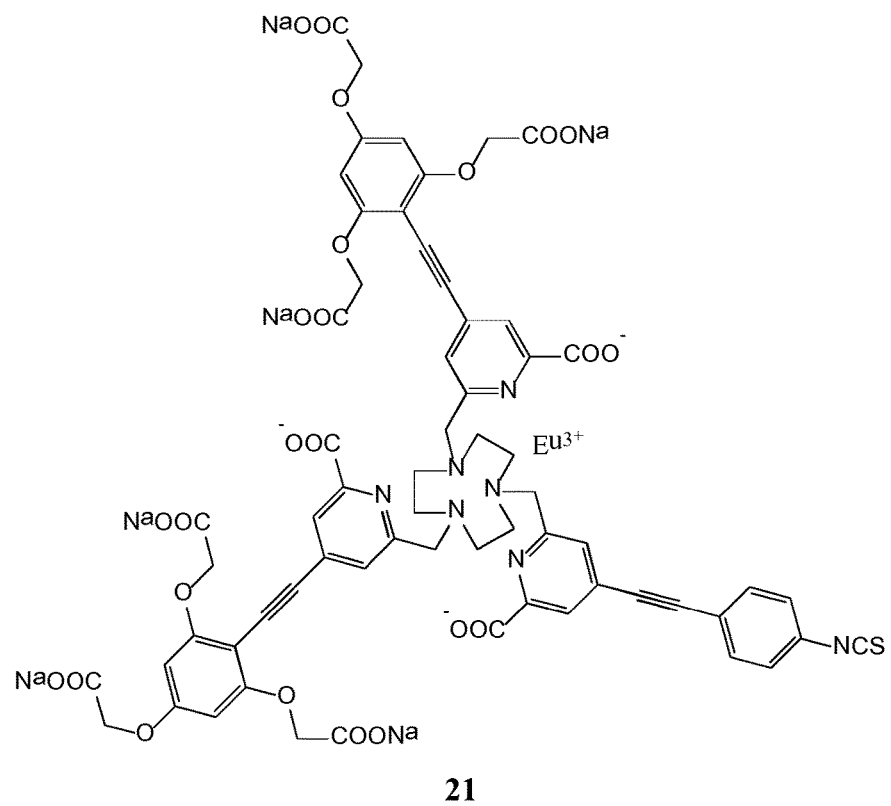
Figure 8:
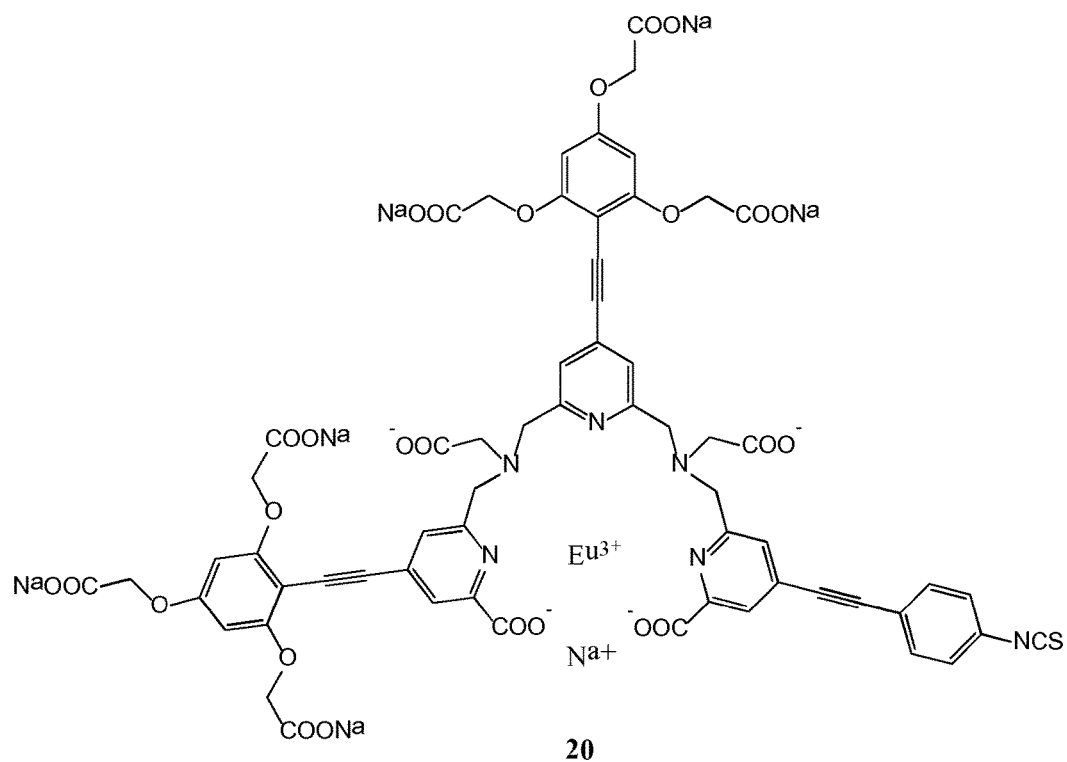
Figure 9:
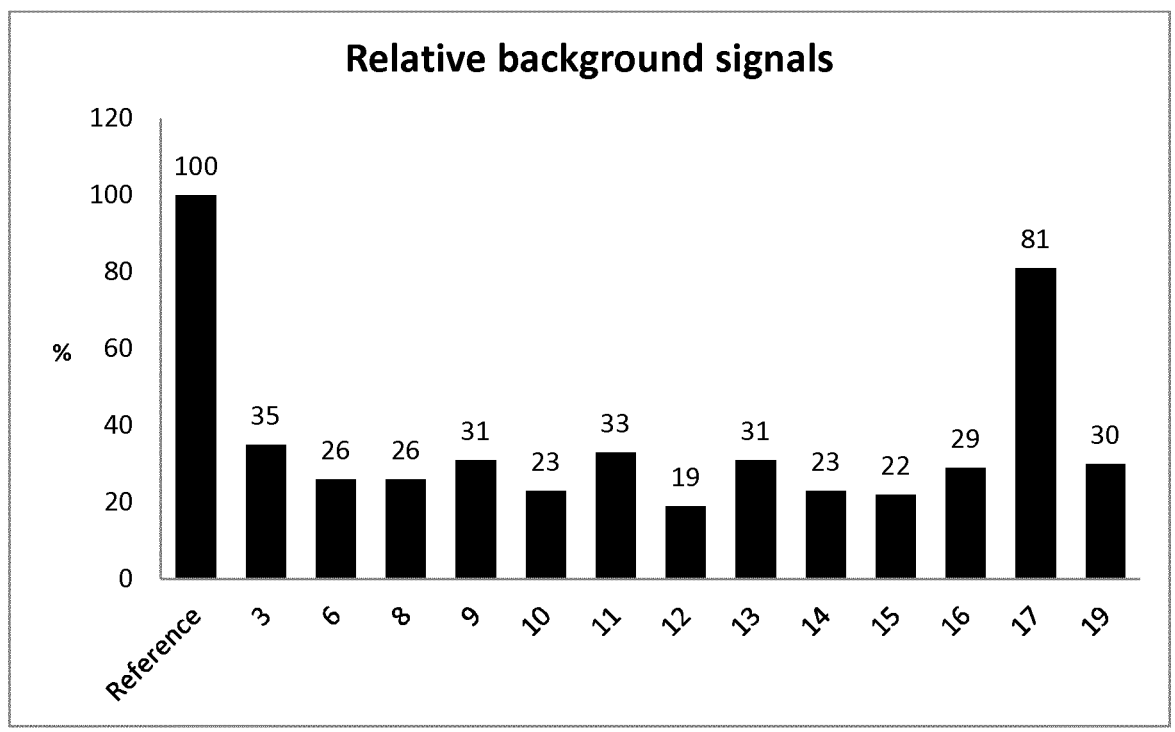

FIG. 1 shows Scheme 1.
FIG. 2 shows Scheme 2.
FIG. 3 shows Scheme 3.
FIG. 4 shows Scheme 4.
FIG. 5 shows Scheme 5.
FIG. 6 shows Scheme 6.
FIG. 7 shows Scheme 7.
FIG. 8 shows Scheme 8.
FIG. 9 shows the relative background signals of different background blockers.

DETAILED DISCLOSURE OF THE INVENTION

The present invention concerns a background blocking reagent for use in time-resolved fluorometry (TRF) binding assays such as bio-affinity assays comprising lanthanide chelate(s) or chelating ligand(s).

The present invention utilizes the discovery that background luminescence in TRF binding assays can be reduced significantly by using the same or similar chelating ligand structure in blocking agents as used for chelating the fluorescent lanthanide ion used to label the specific binding component, e.g. a biomolecule, such as an antibody, in the assay. The chelating ligand may be used as such or as a chelate comprising a suitable coordination lanthanide ion. The present invention thus provides background blocking reagents which prevent non-specific binding of the fluorescent labelled analyte-specific binding component(s) on the surface of the assay support in use.

The term "sample" means in the context of the present invention a biological sample (such as blood, serum, plasma, urine, oral fluid, stool, cerebrospinal fluid, amniotic fluid, cervical fluid, tissue fluid, tissue homogenate, sweat, semen, milk, wound fluid, ascites, etc.), a sample from environmental studies (waste water, soil samples, leachate), a sample from industrial processes (process solutions, products) and compound libraries (screening libraries which may comprise organic compounds, natural products, biological extracts, native, synthetic and recombinant proteins and peptides, nucleotides, and the like).

The term "biomolecule" means in the context of the present invention a natural or synthetic biological compound preferably selected from a polyclonal or monoclonal antibody which may be genetically or chemically modified, antigen, protein, peptide, glycoprotein, sugar, oligosaccharide, polysaccharide, nucleotide sequence, such as a DNA, RNA or PNA probe, hapten, lectin, enzyme, receptor, aptamers, molded plastic imprint (molecular imprinting), and the like.

The term "analyte" means in the context of the present invention a molecule, in particular a biomolecule, of specific interest to be detected in a sample. Examples of analytes of interest are antibodies, antigens, enzymes, hormones, proteins and glycoproteins, such as membrane receptors and membrane markers, DNA and RNA nucleotide sequences, and the like.

The term "analyte-specific binding component" means in the context of the present invention a binding molecule or ligand, in particular a biomolecule, which binds specifically to said analyte. The term "first analyte-specific binding component" refers to the analyte-specific binding component being immobilized on the solid support. The term "second analyte-specific binding component" refers to the analyte-specific binding component being labelled with a lanthanide chelate.

The term "non-specific component" means that said component is not recognized by the analyte(s), the immobilized first analyte-specific binding biomolecule(s) or the labelled second analyte-specific binding component(s).

The term "analyte analogue" means in the context of the present invention a derivative, a fusion, or a mutant of a biomolecule, or the like.

In a first aspect of the present invention, the new principle of using a blocking agent similar to labelling agent finds use in a binding assay for detecting one or more specific analyte(s) in a sample comprising:
a) providing a first analyte-specific binding component or a set of different first analyte-specific binding components immobilized onto a coated or uncoated solid support;
b) adding to said solid support:
   1) a second analyte-specific binding component labelled with a luminescent lanthanide chelate or a set of different second analyte-specific binding components being specific to said different analytes, each binding component being labelled with a different luminescent lanthanide chelate comprising a different lanthanide ion;
   2) a non-specific reagent, which is non-specific to the said analyte(s) and to said first and second analyte-specific binding components and is selected from:
      i) a biomolecule labelled with a lanthanide chelate, wherein said biomolecule is non-specific to said analyte(s) and to said first and second analyte-specific binding components, and the lanthanide ion is different from the lanthanide ion(s) in the said lanthanide chelate labelled analyte-specific binding component(s),
      ii) a biomolecule labelled with a chelating ligand, wherein said biomolecule is non-specific to said analyte(s) and to said first and second analyte-specific binding components, and no lanthanide ion is present,
      iii) a lanthanide chelate comprising no biomolecule, wherein the lanthanide ion is different from the lanthanide ion(s) in said lanthanide chelate labelled analyte-specific binding component(s), or
      iv) a chelating ligand comprising no biomolecule and no lanthanide ion,
   3) the sample; and
c) detecting the specific analyte(s) by time-resolved fluorometry (TRF).

The non-specific reagent may be added before, at the same time as or after said labelled analyte-specific binding component(s) has been added. Depending on the assay this could be performed by adding the labelled analyte-specific binding component(s) in, e.g., the incubation buffer, the sample, or washing fluid.

In a preferred embodiment, the chelating ligands used to label the analyte-specific binding component(s) and used in the non-specific reagent have the same or similar structure. More preferably, the chelating ligands used to label the analyte-specific binding component(s) and used in the non-specific reagent have an identical structure. The analyte-specific binding component(s) is/are, however, replaced by a non-specific biomolecule, such as a nonsense antibody or another protein, in the non-specific reagent, or totally absent in the non-specific reagent. The chelated lanthanide ion in the non-specific reagent is different from the lanthanide ion(s) used to label the analyte-specific binding component (s). When different labelled analyte-specific binding components are used to detect different specific analytes in the same assay, the chelating ligands may be the same or different, but it is preferred that they are the same. The lanthanide ions are different for each different labelled analyte-specific binding component. The chelating ligand may also be used as such as the non-specific reagent without any coordination ion with or without a non-specific biomolecule. In a most preferable embodiment the non-specific reagent is not conjugated to a biomolecule and is without a coordination ion. Moreover, it is preferred that the non-specific reagent has at least one cyclic chelating moiety.

According to one embodiment of the assay of the present invention, the non-specific reagent is added to the solid support onto which one or more analyte-specific biomolecule(s) is/are immobilized for capturing one or more specific analyte(s), followed by addition of the analyte-specific binding component labelled with a luminescent lanthanide chelate or a set of different analyte-specific binding components specific to different analytes, each binding component being labelled with a different luminescent lanthanide chelate comprising a different lanthanide ion. After addition of the sample, the solid support is incubated and washed. In another embodiment, the non-specific reagent and the labelled analyte-specific binding component(s) are added to the solid support at the same time, before or after the sample. In a further embodiment, the labelled analyte-specific component(s) is/are added to the solid support after an addition of the non-specific reagent, the sample and washings.

According to another embodiment of the assay of the present invention, the second analyte-specific binding component is replaced by an analyte labelled with a luminescent lanthanide chelate or a set of different labelled analytes, each analyte being labelled with a different luminescent lanthanide chelate comprising a different lanthanide ion, and wherein the non-specific reagent is selected from:

v) an analyte analogue(s) labelled with a second lanthanide chelate, wherein said analyte analogue(s) is/are not recognized by the first analyte-specific binding component (s), and the lanthanide ion(s) is/are different from the lanthanide ion(s) in said luminescent lanthanide chelate labelled analyte, vi) a chelating ligand labelled analyte analogue(s), wherein the analyte analogue(s) is/are not recognized by the first analyte-specific binding component(s), and no lanthanide ion is present, vii) a second lanthanide chelate comprising no analyte analogue and the lanthanide ion(s) is/are different from the lanthanide ion(s) in said lanthanide chelate labelled analyte(s), or viii) a chelating ligand comprising no analyte analogue(s) and no lanthanide ion(s).

The assay may comprise further steps, such as one or more extra washing steps, one or more incubation steps, one or more thermocycling steps, one or more drying step(s), and the like, adapted to the selected particular binding assay, which additional steps are known by and trivial to a person skilled in the art.

In a second aspect of the present invention, the new principle of using a blocking reagent similar to a labelling agent finds use in a kit for use in detecting one or more specific analyte(s) in a binding assay, comprising:

a) a first analyte-specific binding component or a set of different first analyte-specific binding components specific to different specific analytes, immobilized onto a coated or uncoated solid support;

b) a second analyte-specific binding component labelled with a lanthanide chelate or a set of different second analyte-specific binding components being specific to said different analytes, each binding component being labelled with a different luminescent lanthanide chelate comprising a different lanthanide ion; and c) a non-specific reagent, which is non-specific to the said analyte(s) and to said first and second analyte-specific binding components, and is selected from:
  i) a biomolecule labelled with a lanthanide chelate, wherein said biomolecule is non-specific to said analyte(s) and to said first and second analyte-specific binding components, and the lanthanide ion is different from the lanthanide ion(s) in the said lanthanide chelate labelled specific binding component (s),
  ii) a biomolecule labelled with a chelating ligand, wherein said biomolecule is non-specific to said analyte(s) and to said first and second analyte-specific binding components, and no lanthanide ion is present,
  iii) a lanthanide chelate comprising no biomolecule, wherein the lanthanide ion is different from the lanthanide ion(s) in said lanthanide chelate labelled specific binding component(s), or
  iv) a chelating ligand comprising no biomolecule and no lanthanide ion.

The kit is suitable for use in the assay according to the first aspect of the present invention. The chelates/chelating ligands to be included in the kit are selected to be used in the assay according to the first aspect of the invention.

In one embodiment of the first and second aspect of the invention, the first analyte-specific binding component(s) is/are immobilized directly onto the solid support. In another embodiment, the first analyte-specific binding component(s) is/are immobilized onto the solid support via a specific binding pair, such as biotin-streptavidin, biotin-avidin or other suitable pairs known in the art, where one member of the pair is bound to said first analyte-specific binding component(s) and the other member is immobilized on the solid support. Linkers may also be applied in the immobilization if desirable such as for example for spatial reasons.

In a third aspect, the present invention concerns the use of a background blocker in a binding assay for detecting one or more specific analyte(s) by time-resolved fluorometry (TRF), said assay comprising a first analyte-specific binding component or set of different first analyte-specific binding components immobilized on a solid support and a second analyte-specific binding component labelled with a lanthanide chelate or a set of different second analyte-specific binding components being specific to said different specific analytes, each binding component being labelled with a different luminescent lanthanide chelate comprising a different lanthanide ion, wherein the background blocker is a non-specific reagent, which is non-specific to the said analyte(s) and to said first and second analyte-specific binding components and is selected from:

i) a biomolecule labelled with a lanthanide chelate, wherein said biomolecule is non-specific to said analyte(s) and to said first and second analyte-specific binding components, and the lanthanide ion is different from the lanthanide ion(s) in the said lanthanide chelate labelled specific binding component(s), ii) a biomolecule labelled with a chelating ligand, wherein said biomolecule is non-specific to said analyte(s) and to said first and second analyte-specific binding components, and no lanthanide ion is present, iii) a lanthanide chelate comprising no biomolecule, wherein the lanthanide ion is different from the lanthanide ion(s) in said lanthanide chelate labelled specific binding component(s), or iv) a chelating ligand comprising no biomolecule and no lanthanide ion.

In a fourth aspect, the present invention concerns the use of a background blocking reagent in the preparation of a kit for use in a binding assay for detecting one or more specific analyte(s) by time-resolved fluorometry (TRF) said assay comprising a first analyte-specific binding component or set of different first analyte-specific binding components immobilized on a solid support and a first analyte-specific binding component labelled with a lanthanide chelate or a set of different first analyte-specific binding components being specific to said different specific analytes, each binding component being labelled with a different luminescent lanthanide chelate comprising a different lanthanide ion, wherein the background blocker is a non-specific reagent, which is non-specific to the said analyte(s) and to said first and second analyte-specific binding components, and is selected from:
  i) a biomolecule labelled with a lanthanide chelate, wherein said biomolecule is non-specific to said analyte (s) and to said first and second analyte-specific binding components, and the lanthanide ion is different from the lanthanide ion(s) in the said lanthanide chelate labelled specific binding component(s),
  ii) a biomolecule labelled with a chelating ligand, wherein said biomolecule is non-specific to said analyte(s) and to said first and second analyte-specific binding components, and no lanthanide ion is present,
  iii) a lanthanide chelate comprising no biomolecule, wherein the lanthanide ion is different from the lanthanide ion(s) in said lanthanide chelate labelled specific binding component(s), or
  iv) a chelating ligand comprising no biomolecule and no lanthanide ion.

More particular, the chelate ligand for use in the present invention comprises pyridine moieties of the formula (I) having from seven to ten coordinating heteroatoms towards a lanthanide (Ln), if said lanthanide is present:

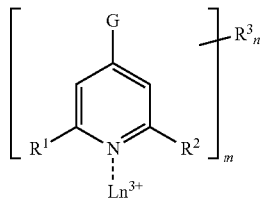

I m is a positive integer from 1 to 5 and the dashed line represents a coordination bond between the pyridine nitrogen and the lanthanide ion, if said lanthanide ion is present.

The said chelate or chelating ligand comprising 1-5 pyridine moieties of formula I contains 1-5 of the same or different group G, which are selected from i) a conjugating group, ii) a single bond, and iii) hydrogen.

G is substituted with electron with-drawing and/or electron-donating groups. The electron with-drawing groups can be, but not limited to —$NO_2$, —CN, —$SO_3H$, —COOH, —CHO, —$COR^5$, —$CF_3$, —$N^+(CH_3)_3$ and halogen (i.e. —F, —Cl, —Br and —I). G is preferably substituted with electron-donating groups which can be, but are not limited to —$C_{1-6}$ alkyl or —X—$(R^4)_{1-2}$ wherein X is an oxygen atom, a sulfur atom, a nitrogen atom, or —$N(R^5)CO$—, wherein $R^5$ is hydrogen or —$C_{1-6}$ alkyl, and $R^4$ is selected from hydrogen, —$C_{1-6}$alkyl, —$(CH_2)_{1-6}OH$, —$(CH_2)_{1-6}$ $OC_{1-6}$ alkyl, —$(CH_2)_{1-6}CO_2H$, —$(CH_2)_{1-6}CONR^6R^7$, —$(CH_2)_{1-6}CO$(piperazin-1,4-diyl)$(CH_2)_{1-6}COOH$, —$(CH_2)_{1-6}SO_3H$, —$(CH_2)_{1-6}NH_2$, —$(CH_2)_{1-6}N(CH_3)_2$, —$(CH_2)_{1-6}N^+$—$(CH_3)$—$(CH_2)_{1-6}SO_3^-$, —$(CH_2)_{1-6}NH$ $(CH_2)_{1-6}COOH$, —$(CH_2)_{1-6}N(CH_3)(CH_2)_{1-6}COOH$ and polyethylene glycol, wherein $R^6$ and $R^7$ are each independently selected from hydrogen, $C_{1-6}$alkyl, —$(CH_2)_{1-6}OH$, —$CH(CH_2OH)_2$, and —$CH(CH_2OH)_3$, —$CH_2[CH(OH)]_{1-6}$ $CH_2OH$.

The conjugating group consists of one, two or three moieties, each moiety being selected from ethenylene (—CH=CH—), ethynediyl (—C≡C—), carbonyl (—C(=O)—), and biradicals of (hetero)aromatic ring or ring systems (-Het/Ar—), such as for example phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene, and oxadiazolylene.

Each of $R^3_n$, in which n is a positive integer from 1 to 5, is independently selected from i) a covalent group $Z^1$ formed from a reactive group $Z^2$ and a corresponding group in a biomolecule after coupling to the said biomolecule, ii) a hydrophobic group, iii) a hydrophilic group, and iv) hydrogen.

The reactive group $Z^2$ is facilitating the conjugation to a non-specific biomolecule, or is facilitating the formation of a covalent bond to other reagents (e.g. diaminohexane; see examples section) or a polymer.

Examples of the reactive group are those selected from azido (—$N_3$), alkynyl (—C≡CH), alkylene (—CH=$CH_2$), amino (—$NH_2$), aminooxy (—O—$NH_2$), carboxyl (—COOH), aldehyde (—CHO), mercapto (—SH), maleimido groups or activated derivatives thereof, including isocyanato (—NCO), isothiocyanato (—NCS), diazonium (—$N^+$≡N), bromoacetamido, iodoacetamido, reactive esters, pyridyl-2-dithio, and 6-substituted 4-chloro-1,3,5-triazin-2-ylamino.

The substituents in 6-substituted 4-chloro-1,3,5-triazin-2-ylamino can be selected from the group consisting hydrogen, halogen, alkoxy, aryloxy, amino, alkyl with one to six carbon atoms, substituted amino or thioethers, and preferable selected from the group consisting of chloro, fluoro, ethoxy, 2-methoxyethoxy, 2-cyanoethoxy, 2,2,2-trifluoroethoxy, thiophenoxy or ethoxycarbonyl-thiomethoxy. The substituted amino or thioether is preferable mono- or disubstituted each substituent being preferable independently selected from the group consisting of an alkyl or alkoxy with one to six carbon atoms, phenyl, carbonyl or carboxyl.

It follows that upon reaction with a non-specific biomolecule or other reagents (such as 1,6-diaminohexane) or a polymer, the reactive group $Z^2$ establishes a link to said non-specific biomolecule or said other reagents or said polymer, e.g. of one of the following types: a thiourea (—NH—C(=S)—NH—), an aminoacetamide (—NH—CO—$CH_2$—NH—), an amide (—NH—CO—, —CO—NH—, —$NCH_3$—CO— and —CO—$NCH_3$—), and aliphatic thioether (—S—), a disulfide (—S—S—), a 6-substituted-1,3,5-triazine-2,4-diamine, a

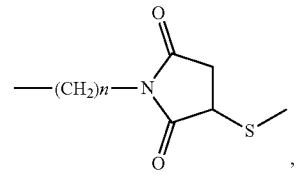

wherein n=1-6; and a triazole (e.g. formed by the so-called "click" chemistry).

Hydrophobic group increases the non-specific binding properties of the said chelate or chelating ligand and can be selected from 1-6 combinations of following groups such as alkyls with 1-20 carbon atoms, and additionally 0 to 4 other atoms such as oxygen, sulfur and nitrogen (such as —$(CH_2)_{0-20}CH_3$, —$NH(CH_2)_{1-20}NH_2$, —$NH(CH_2)_{1-6}O$ $(CH_2)_{1-6}NH_2$, —$NH[(CH_2)_{2-6}O]_{1-10}(CH_2)_{1-6}NH_2$, —NH $(CH_2)_{1-6}NH(CH_2)_{1-6}NH_2$) aryl, biaryl (such as phenyl, biphenyl naphtyl) or oligopeptide having 1-20 amino acid residues.

Examples of hydrophilic groups are mono- and oligosaccharides, such as monosaccharides and disaccharides, oligoalkylene glycols (e.g. those having 1-20 repeating units) such as 20 oligoethylene glycol and oligopropylene glycol, etc.

In one embodiment, the hydrophilic group is selected from monosaccharides, disaccharides, —$(CH_2)_{1-6}CH_2OH$, —$CH(CH_2OH)_2$, —$C(CH_2OH)_3$—$(CH_2)_{1-3}$—O—$(CH_2CH_2O)_{0-5}$—H, —$(CH_2)_{1-3}$—O—$(CH_2CH_2O)_{0-5}$—$C_{1-4}$-alkyl, —O—$(CH_2CH_2O)_{1-6}$—H, and —O—$(CH_2CH_2O)_{1-6}$—$C_{1-4}$-alkyl, in particular monosaccharides.

In the present context, the term "monosaccharide" is intended to mean $C_5$-$C_7$ carbohydrates being either in the acyclic or in cyclic form. Examples of monosaccharides are $C_6$ carbohydrates, e.g. those selected from

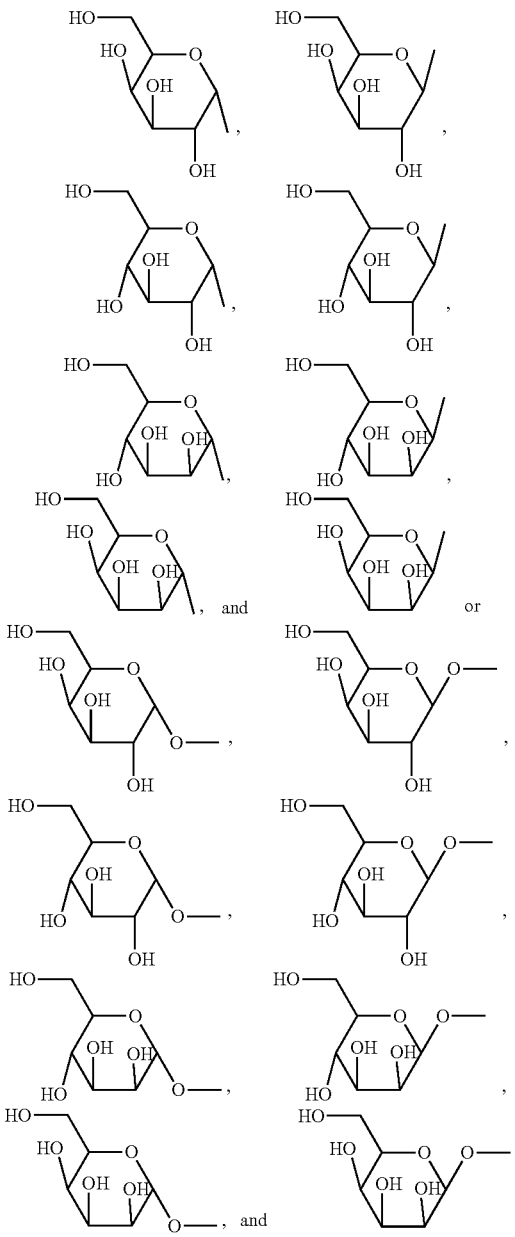

In the present context, the term "disaccharide" is intended to mean two monosaccharides (cf. above) linked together, preferably via glycosidic bonds.

$R^1$ and $R^2$ represent i) additional chelating moieties Ch forming one or more coordination bond between the said heteroatoms and lanthanide, if said lanthanide is present, ii) a bond between the said pyridine moiety and other moieties of the compound, or iii) a bond between individual pyridine moieties of the formula (I).

Preferably, either $R^1$ or $R^2$ is a chelating group Ch forming coordination bonds with $Ln^{3+}$ ion, and can be but is not limited to groups such as —$COO^-$, —$PO_3^{2-}$, —$PMeO_2^-$, —$PPhO_2^-$, —$CH_2PO_3^{2-}$. One $R^1$ or $R^2$ in the 1-5 pyridine moieties could be —$CONHR^9$ or —$CONR^9R^{10}$, in which $R^9$ or $R^{10}$ is an alkyl group or a linker group containing the reactive group for covalent coupling to the biomolecule or a covalent group $Z^1$ formed from the said reactive group $Z^2$ and corresponding group in the biomolecule after coupling reaction.

Moreover, $R^1$ and $R^2$ each represent a bond between the chromophoric moiety and other moieties of the chelate, e.g. chromophoric moieties and chelating moieties. The chelating moiety comprising at least two carboxylic acid or phosphoric acid groups, esters, amides or salts of said acids, attached to an aromatic unit of the chromophoric moiety, either directly or via a cyclic or acyclic N- and/or O-containing hydrocarbon chain. The said other moiety can contain a linker group containing the group $R^3$.

Specific bio-affinity based binding assays utilizing fluorometric or time-resolved fluorometric determination of specific luminescence include immunoassays (both homogeneous and heterogeneous), nucleic acid hybridization assays, receptor-binding assays, enzymatic assays, immunocytochemical assays, immunohistochemical assays and cell based assays. The blocking reagent of the present invention provides a means for obtaining improved assay sensitivity.

In one embodiment of the present invention, $Ln^{3+}$ chelated in the blocking reagent is a lanthanide ion or an yttrium ion and the lanthanide ion is selected from $Gd^{3+}$, $La^{3+}$, $Lu^{3+}$, $Pr^{3+}$, $Nd^{3+}$, $Ho^{3+}$, $Er^{3+}$ and $Yb^{3+}$.

In another embodiment of the present invention, the group $Ln^{3+}$ is absent in the blocking reagent.

If a chelated lanthanide is used in the blocking agent, it must be different from the lanthanides used in the labelled analyte-specific binding component or set of different labelled analyte-specific binding components. If different analyte-specific binding components are used in the same assay to detect different specific analytes, they are labelled with different chelated lanthanides.

It has surprisingly been observed that $Gd^{3+}$ chelates increase specific $Eu^{3+}$ emission signal by energy transfer from the $Gd^{3+}$ chelate to the nearest situated $Eu^{3+}$ chelate. Thus, in a preferred embodiment $Eu^{3+}$ is used to label the specific biomolecule and $Gd^{3+}$ is used in the blocking reagent. The blocking reagent may or may not comprise a conjugated non-specific biomolecule. It was even more surprising that a chelating ligand without any coordination ion and conjugation to a non-specific biomolecule reduces significantly the background. Therefore, in a most preferable embodiment the non-specific reagent is not conjugated to the said non-specific biomolecule and is without any coordination ion, and moreover, the non-specific reagent has a cyclic chelating moiety.

Lanthanides having an detectable emission wavelength (such as $Eu^{3+}$, $Tb^{3+}$, $Sm^{3+}$, $Dy^{3+}$, $Nd^{3+}$, $Er^{3+}$, $Ho^{3+}$, $Tm^{3+}$ and $Yb^{3+}$) can be used to label the specific biomolecule and any of other lanthanides which do not have an emission band at the emission wavelength of the labeled specific biomolecule could be used in the blocking reagent. Moreover, the other fluorescent lanthanides could be used as internal assay or measurement controls. For example, the other fluorescent lanthanide can be conjugated to biotin and immobilized to a streptavidin coated surface. The signal of other fluorescent lanthanide on the immobilized surface and the signal from the known amount of analyte, i.e. the obtained two different emission signals after TRF-measurements, can be used to adjust various individual instruments to give same signal levels from the same amount of samples or liquid controls using a known relation between the different emissions of the biotin conjugated other fluorescent lanthanide and the fluorescent lanthanide used to measure the analyte in the sample or liquid control.

In a further embodiment of the present invention, $Ln^{3+}$ is a lanthanide ion or an yttrium ion and the lanthanide ion is selected from $Gd^{3+}$, $La^{3+}$, $Lu^{3+}$, $Pr^{3+}$, $Nd^{3+}$, $Ho^{3+}$, $Er^{3+}$ and $Yb^{3+}$, and one $R^3$ group is a covalent group $Z^1$ formed from a reactive group $Z^2$ and a corresponding group in a non-specific biomolecule after coupling to the said biomolecule.

In yet another embodiment of the present invention, the group $Ln^{3+}$ is absent and one $R^3$ group is a covalent group $Z^1$ formed from a reactive group $Z^2$ and a corresponding group in a non-specific biomolecule after coupling to the said biomolecule.

In a preferred embodiment, a $Eu^{3+}$ chelate is used to label the analyte-specific compound and a $Gd^{3+}$, $La^{3+}$, $Lu^{3+}$, $Pr^{3+}$, $Nd^{3+}$, $Ho^{3+}$, $Er^{3+}$, $Yb^{3+}$ or $Y^{3+}$ chelate is used as the blocking agent, where the chelating ligand in the label and the blocking agent is the same or structurally similar. In a more preferred embodiment, a $Eu^{3+}$ chelate is used to label the specific biomolecule and a $Gd^{3+}$ chelate is used as the blocking agent, where the chelating ligand in the label and the blocking agent is the same or structurally similar. In a most preferable embodiment a $Eu^{3+}$ chelate is used to label the specific biomolecule and a chelating ligand is used as the blocking agent, where the blocking agent is same or structurally similar, and has a cyclic or acyclic chelating moiety.

Non-limiting examples of pyridine moieties of the formula (I) are shown below:

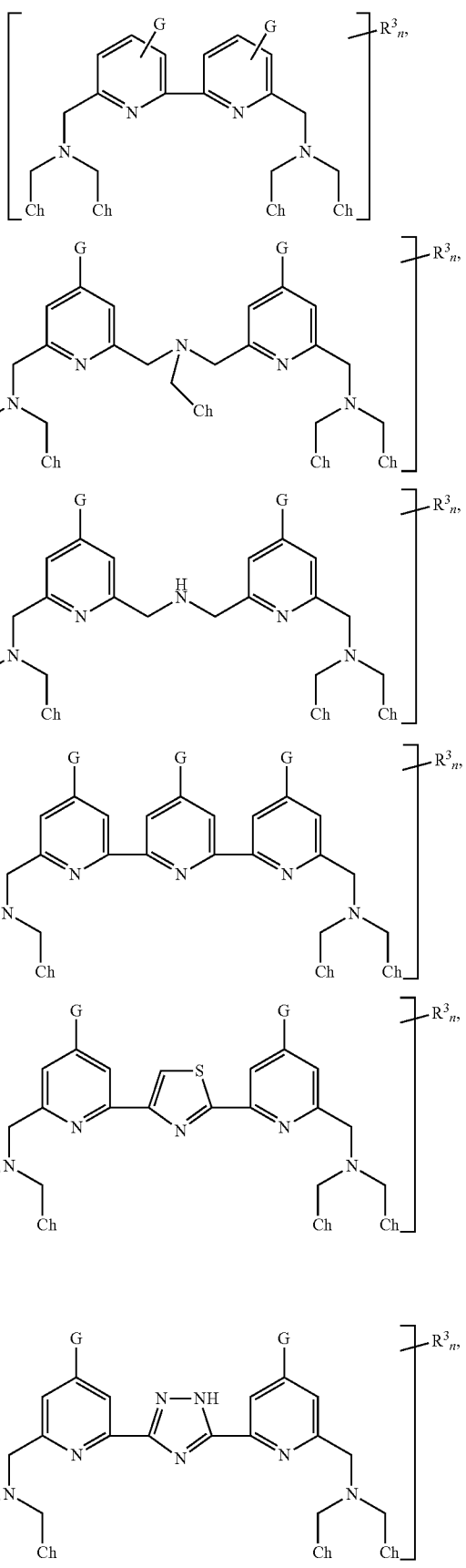

-continued

-continued
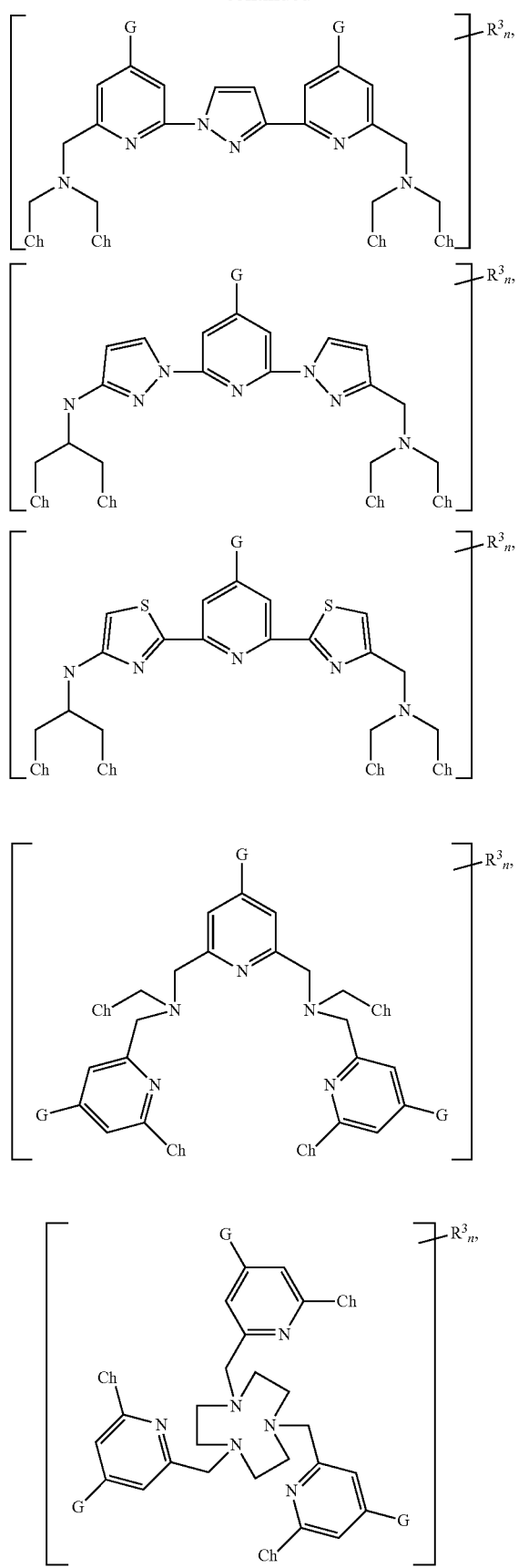
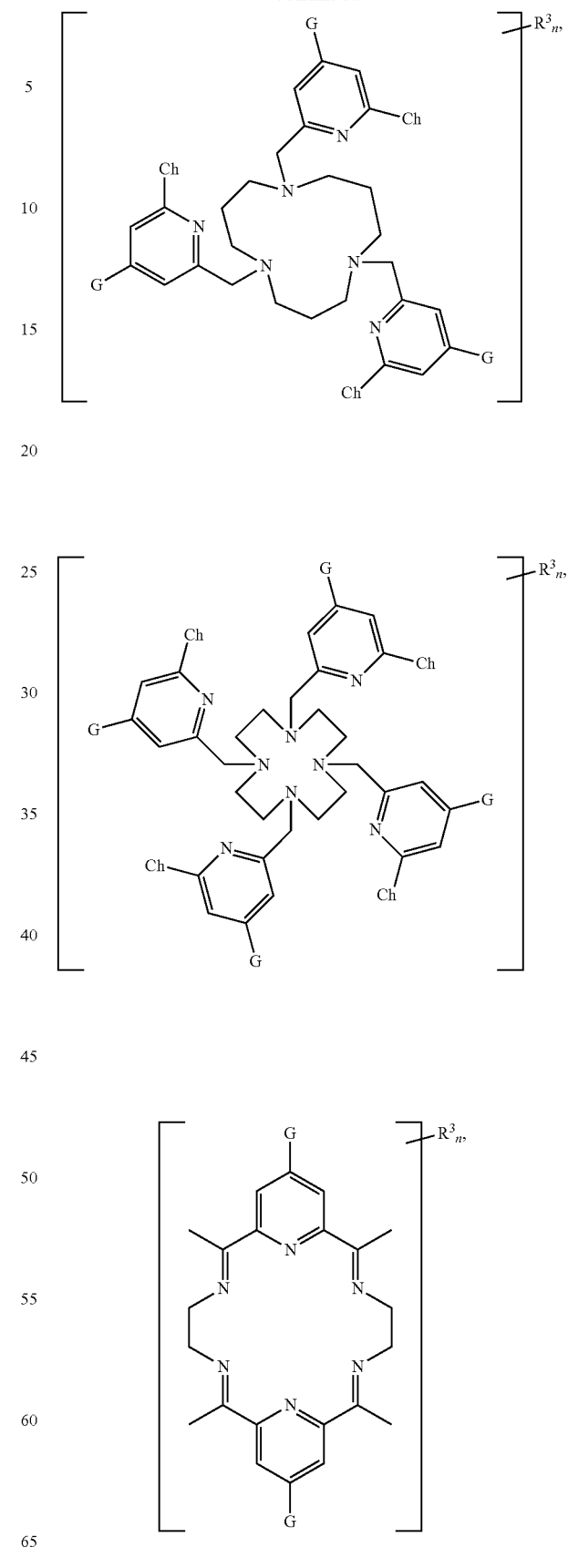

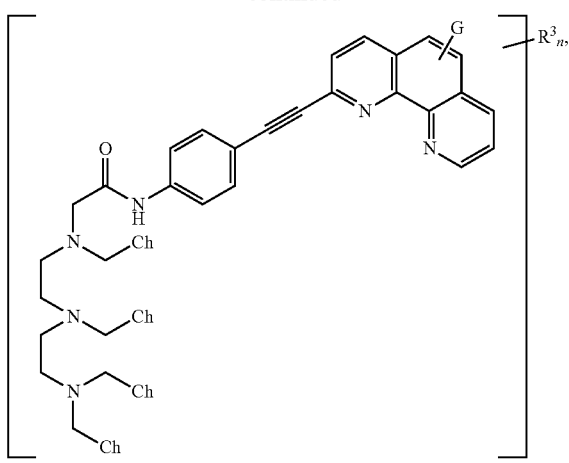

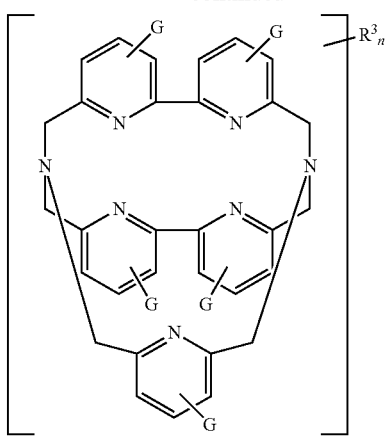

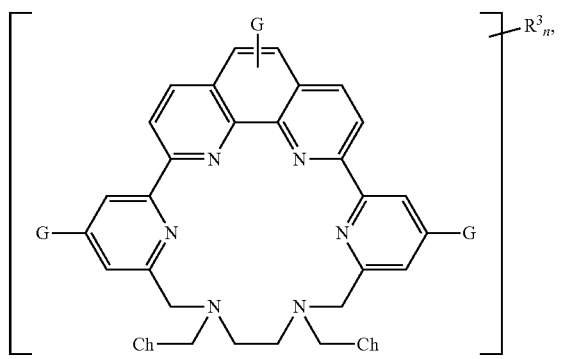

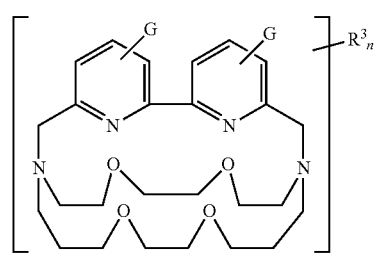

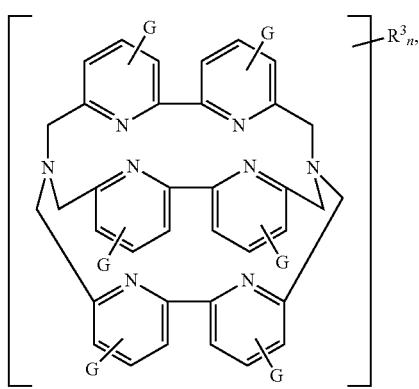

Besides of the pyridine based compounds e.g. various phenolic (e.g. Bailey, M. P., et al. Analyst 1984, 109, 1449; U.S. Pat. No. 4,670,572; Kankare, J., et al., Anal. Chim. Acta 1992, 266, 205; WO 2000/048991 and WO 2008/063721), 1,2-hydroxypyridinone (e.g. WO 2008/008797) compounds and DTPA carbosyril 124 conjugates (Selvin, P. R., et al., J. Am. Chem. Soc. 1994, 16 6029) can be used for the purpose.

An example of a "pair" of chelates comprising a reactive group for coupling of a specific biomolecule ($Ln^{3+}=Eu^{3+}$) and a non-specific biomolecule ($Ln^{3+}=Gd^{3+}$) respectively for use in a TRF binding assay according to the present invention is shown below.

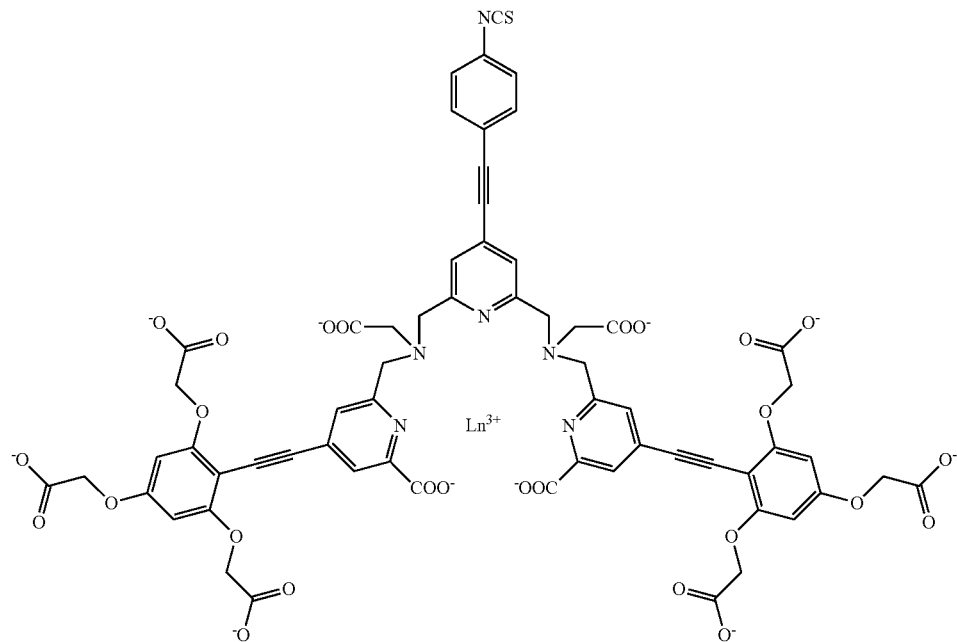

The analyte-specific biomolecule(s) is/are typically immobilized on the solid support either covalently or non-covalently. In one embodiment, the analyte-specific biomolecule(s) is/are immobilized directly on the solid support. In another embodiment, the analyte-specific biomolecule(s) is/are immobilized via a binding pair, such as biotin-streptavidin, biotin-avidin and the like, where one member of the pair is bound to the analyte-specific biomolecule(s) and the other immobilized on the solid support. Linkers may be applied in the immobilization if desirable for example spatial reasons.

The assay solid support is water insoluble particles and surfaces such as polystyrene surfaces, polymer beads, glass beads, gold particles, nanoparticles, tissue, tissue fragments, cells, etc., selected to suit the specific binding assay in the best way. The solid support may be selected from a nanoparticle, a microparticle, a slide, a plate, and a solid phase synthesis resin. Such solid supports are known to and can easily be selected and used by the person skilled in the art. As an example may be mentioned microtiter plates. The different assay formats may comprise further components for preparing said assay. The kit may also comprise instructions for use of the content in a suitable assay according to the invention.

Chelating ligands can be obtained and used to prepare lanthanide chelates with lanthanide coordination ions as described in the prior art discussed above. The chelates and chelating ligands may also be conjugated to the analyte-specific binding component or the set of different analyte-specific binding components or non-specific reagent as disclosed in the prior art. For example, activated chelates and activated chelating ligands for use as blocking reagents can be coupled with a nonsense IgG antibody by using excess amounts of the chelate/ligand as described by von Lode, P. et al. in Anal. Chem., 2003, 75, 3193-3201. The coupling reaction is carried out overnight at room temperature and the product is separated from the excess of reagent, for example on a suitable gel filtration column and the fractions containing the antibody are pooled. The conjugated chelate/ligand concentrations can be measured using UV absorbance at different specific wavelengths. The amount of coupled chelates/ligands per antibody will typically vary on average between 1 and 50, particularly between 2 and 40, more particularly between 5 and 30, such as between 10 and 15.

The assay background with and without the blocking reagents of the invention was compared in a Troponin I (TnI) sandwich immunoassay, where a tracer antibody labeled with the $Eu^{3+}$ chelate comparable to the structure of a $Gd^{3+}$ chelate was used. The tracer antibody and a TnI standard solution were pipetted to pre-coated assay wells coated with streptavidin and a biotinylated capture antibody against TnI and the compounds to be tested. The reaction mixtures were incubated followed by washing and dried prior to measurement with a fluorometer. A significant decrease of background signal was seen. Surprisingly high increases in specific signal, even up to 40%, were observed with different blocking reagents described in this application.

It is worth noticing that even when using strongly chelating ligands as blocking reagents in high concentrations compared to the luminescent chelates used in the assay, a significant background reduction comparable to the use of an Ln-based blocking reagent, for example a $Gd^{3+}$-based blocking reagent was obtained and it has no negative effect to the obtained specific signals.

As a whole, the background blocking principle of the present invention can be effectively applied by using individual chelates and ligands, chelates and ligands conjugated to antibodies, ligands conjugated to a polymer, ligands conjugated to an organic molecule (hydrophobic group) and ligands conjugated to a hapten such biotin, and thus, ligands immobilized to a streptavidin coated surface.

EXPERIMENTAL SECTION

The following non-limiting examples are aimed to further demonstrate the invention. The structures and synthetic routes employed are presented in Schemes 1-8. Scheme 8 presents the $Eu^{3+}$ chelates (20 and 21) used for antibody tracer labeling needed in the immunoassay tests.

EXAMPLES $^1$H-NMR spectra were recorded with Bruker AVANCE DRX 500 MHz. Tetramethyl silane was used as internal reference. Mass spectra were recorded PerSeptive Biosystems Voyager DE-PRO MALDI-TOF instrument using α-cyano-4-cinnamic acid matrix. UV-Vis spectra were recorded on Pharmacia Ultrospec 3300 pro. Fluorescence measurements was performed with a Perkin-Elmer Wallac Victor™ plate fluorometer and immunoassay was performed with a Radiometer AQT 90 Flex immunoassay analyzer.

Conditions for HPLC purification runs: Reversed phase HPLC (RP-18 column). The solvents were A: triethyl ammonium acetate buffer (TEAA) (20 mM, pH7) and B: 50% acetonitrile in triethyl ammonium acetate buffer (20 mM, pH7). The gradient was started from 5% of solvent B and the amount of solvent B was linearly raised to 100% in 30 minutes.

Column chromatography was performed with columns packed with silica gel 60 (Merck). FC=Flash chromatography, RT=room temperature.

Example 1. Synthesis of Compound 2 (Scheme 1, FIG. 1)

A mixture of the compound 1 (125 mg, 75 µmol; synthesized as described in WO 2013/026790) and 0.5 M KOH in EtOH (10 ml) was stirred for 30 min at RT and $H_2O$ (5 ml) was added. After stirring for 3 h at RT, EtOH was evaporated, the residue was stirred for 20 h at RT, and the pH was adjusted to ca. 6.5 with 6M HCl. $GdCl_2 \times 6H_2O$ (28 mg, 75 µmol) in $H_2O$ (0.4 ml) was added within 10 min and the pH was maintained at 5-7 with solid $NaHCO_3$. After stirring for overnight at RT, the pH was adjusted to 8.5 with 1 M NaOH, the precipitate was centrifuged and the supernatant evaporated to dryness. The product was dissolved in 20 mmol TEAA buffer (1 ml) and purified with semi-preparative HPLC. Yield: 116 mg (72%). $R_t$(HPLC)=15.7 min. UVA/IS=357 nm. MALDI TOF-MS mass: calculated $(M+2H^+)$ 1439.20; found 1439.21.

Example 2. Synthesis of Compound 3 (Scheme 1, FIG. 1)

The pH of an aq. solution (2 ml) of compound 2 (116 mg, 54 µmop was adjusted ca. 7.0-7.5 to with solid $NaHCO_3$, and added within 5 min to a mixture of $CSCl_2$ (58 µl, 0.76 mmol) and $NaHCO_3$ (72 mg, 0.86 mmol) and $CHCl_3$ (2 ml). After stirring for 40 min at RT, the aqueous phase was washed with $CHCl_3$ (3×2 ml). The product was precipitated with acetone (ca. 40 ml), centrifuged, washed with acetone (2×10 ml) and dried.

Example 3. Synthesis of Compound 5 (Scheme 2, FIG. 2)

A mixture of the compound 4 (1.31 g mg, 0.80 mmol; synthesized as described in WO 2016/066641) and 0.5M KOH in EtOH (80 ml) was stirred for 1 h at RT and $H_2O$ (40 ml) was added. After stirring for 4 hours at RT, EtOH was evaporated, and the mixture was stirred for overnight at RT. The pH of the ice-cold mixture was adjusted to ca 2.0-2.5 with 6 M HCl, stirred in ice-bath for 15 min, centrifuged, was with cold $H_2O$ (2×10 ml), cold EtOH (2×10 ml) and dried. Yield: 1.02 g (99%). $R_t$(HPLC)=17.4 min. UVA/IS=346 nm. MALDI TOF-MS mass: calculated $(M+1H^+)$ 1294.34; found 1294.38.

Example 4. Synthesis of Compound 6 (Scheme 2, FIG. 2)

This compound 6 was synthesized from the compound 5 using the method analogous to the synthesis described in the Example 2.

Example 5. Synthesis of Compound 7 (Scheme 3, FIG. 3)

The pH of a suspension of compound 5 (15 mg, 12 µmop in $H_2O$ (5 ml) was adjusted to ca 6.5 with 1 M NaOH. After addition of citric acid (8 mg, 42 µmop in $H_2O$ (0.5 ml), the pH was adjusted to ca. 6.5 with 1 M NaOH. $GdCl_2 \times 6H_2O$ (5 mg, 14 µmol) in $H_2O$ (0.25 ml) was added within 10 minutes and the pH was adjusted to ca. 9.5 with 1M NaOH. The mixture was stirred for 4-6 weeks at 95° C. (until the analytical HPLC chromatogram showed completed complexation). The pH was adjusted to ca. 7.0 with 1M HCl, the mixture was evaporated to dryness, dissolved in 20 mmol TEAA buffer (0.4 ml) and purified with semi-preparative HPLC. $R_t$(HPLC)=15 min. UV=350 nm. MALDI TOF-MS mass: calculated $(M^+)$ 1448.23; found 1448.52 (The product has the same retention time compared to the corresponding $Eu^{3+}$ chelate; see WO 2013/026790).

Example 6. Synthesis of Compound 8 (Scheme 3, FIG. 3)

Compound 8 was synthesized from compound 7 using the method analogous to the synthesis described in the Example 2.

Example 7. Synthesis of Compound 9-15 (Scheme 4, FIG. 4)

A mixture of compound 6 (59 mg, 40 µmol) and respective amine (0.4 mmol) in 50 mM $Na_2CO_3$ buffer (1 ml) was stirred for overnight at RT. The product was precipitated with acetone (40 ml), centrifuged, washed with acetone (2×10 ml) and dried.

TABLE 1

Obtained retention times $R_t$(HPLC) of prepared compounds 9-15.

| Compound | Amine | $R_t$(HPLC)/min |
|---|---|---|
| 9 | $R^7 = CH_2(CH_2)_5NH_2$ | 18.0 |
| 10 | $R^7 = CH_2(CH_2)_9NH_2$ | 22.3 |
| 11 | $R^7 = CH_2CH_2OCH_2CH_2OCH_2CH_2NH_2$ | 17.4 |
| 12 | $R^7 = CH_2CH_2O(CH_2CH_2O)_2CH_2CH_2NH_2$ | 18.1 |
| 13 | $R^7 = CH_2CH_2NHCH_2CH_2NH_2$ | 16.3 |
| 14 | $R^7 = CH_2(CH_2)_7NH_2$ | 19.8 |
| 15 | $R^7 = CH_2CH(OH)CH_2NH_2$ | 16.2 |

Example 8. Synthesis of Compound 16 (Scheme 5, FIG. 5)

Compound 8 (59 mg, 40 µmol) was added to a mixture of polylysine (13 mg, 2 µmol) and in 50 mM $Na_2CO_3$ buffer (1 ml). After overnight reaction, 1,6-diaminohexane (46 mg) was added and the mixture was left to react at RT for overnight. The product was precipitated with acetone (40 ml), centrifuged, washed with acetone (2×10 ml) and dried.

Example 9. Synthesis of Compound 17 (Scheme 6, FIG. 6)

A mixture of compound 6 (73 mg, 50 µmol) and biotin-(PEG)$_4$-NH$_2$ (23 mg, 50 µmol) in 50 mM Na$_2$CO$_3$ buffer (2 ml) was stirred for overnight at RT. After an addition of taurine (13 mg, 0.1 mmo), the mixture was stirred for overnight at RT, and evaporated to dryness. The product was dissolved in 20 mmol TEAA buffer (1 ml) and purified with semi-preparative HPLC. Yield: 10 mg. R$_t$(HPLC)=21.1 min. MALDI TOF-MS mass: calculated (M+1H$^+$+Na$^+$+K$^+$) 1859.55; found 1859.61.

Example 10. Synthesis of Compound 18 and 19 (Scheme 7, FIG. 7)

These two Gd complexes were prepared from the corresponding ligand esters using the methods analogous to the synthesis described in the Example 1 and 2. The esters were prepared using methods and protocols described in WO 2013/026790 and WO 2016/066641.

Example 11. Coupling the Activated Gd Chelates 3, 8, 19 and the Activated Ligand 6 with Anti-Mouse-IgG The general coupling reaction of an anti-mouse-IgG was performed as described by von Lode, P. et al. (Anal. Chem., 2003, 75, 3193-3201), by using 300 fold excess of the used compound 3, 6, 8 or 19. The reactions were carried out overnight at RT. The product was separated from the excess of reactant on Superdex 200 HR 10/30 gel filtration column (GE Healthcare) by using Tris-saline-azide (50 mM Tris, 0.9% NaCl, pH 7.75) buffer as an eluent. The fractions containing the antibody were pooled. The chelate (3, 8, 19) and ligand (6) concentrations were measured using UV absorbance at 350 and 330 nm, respectively. The amount of coupled chelates/ligands per antibody varied on average between 10 and 15.

Example 12. Troponin I Immunoassay and Comparison of the Assay Background with and without the Blocking Reagents of the Invention The background blocking was evaluated in a sandwich immunoassay for the cardiac marker Troponin I. The tracer antibody was labeled with the Eu$^{3+}$ chelate comparable to the structure of Gd$^{3+}$ chelate 3 (see WO 2013/026790). Labelling of the TnI antibody was performed as described by von Lode, P. et al., using 300 folds excess of Eu$^{3+}$ chelate (20 and 21; (Scheme 8, FIG. 8)). The reactions were carried out overnight at RT. Labelled antibody was separated from the excess of Eu$^{3+}$ chelate on Superdex 200 HR 10/30 gel filtration column (GE Healthcare) by using Tris-saline-azide (Tris 50 mM, NaCl 0.9%, pH 7.75) buffer as an eluent. The fractions containing the antibody were pooled and the Eu concentration was measured against Eu standard material on a Victor™ plate fluorometer or by UV absorbance at 340 nm.

A diluted tracer antibody (10 µl, 5 ng/µl) and a TnI standard solution (40 µl) were pipetted into a pre-coated assay well (single wells in 96 well plate format, wells coated with streptavidin and a biotinylated capture antibody against TnI (Innotrac Diagnostics Oy), and the compound to be tested (200 ng/well). The reaction mixtures were incubated 20 min at 36° C. with shaking. The wells were washed 6 times and dried prior to measurement on a Victor™ plate fluorometer. The results are summarized in Table 2 and FIG. 9. In Table 2, both A and B standards were measured in a minimum of 6 replicates. Standard A represents the blank and standard B a mid-range sample concentration.

TABLE 2

Measured absolute signals and calculated mean values, standard deviation and CV for compounds 3 and 8 of the blocking reagents.

| | Compound 3 | | | | Compound 8 | | | |
|---|---|---|---|---|---|---|---|---|
| | No blocking reagent | | Compound 3, 200 ng/well | | No blocking reagent | | Compound 8, 200 ng/well | |
| Standard | A | B | A | B | A | B | A | B |
| Counts_1 | 1412 | 44348 | 424 | 52744 | 3772 | 42444 | 837 | 40781 |
| Counts_2 | 1338 | 50192 | 450 | 52118 | 2093 | 49093 | 1270* | 34908 |
| Counts_3 | 1456 | 47128 | 474 | 51555 | 3186 | 46234 | 795 | 44847 |
| Counts_4 | 1312 | 49942 | 526 | 50679 | 2331 | 46271 | 711 | 40483 |
| Counts_5 | 1542 | 46592 | 416 | 48188 | 2371 | 46984 | 759 | 44553 |
| Counts_6 | 1556 | 54699 | 498 | 44149 | 2719 | 47910 | 909 | 44768 |
| Mean value | 1436 | 48817 | 465 | 49906 | 2745 | 46489 | 802 | 41723 |
| Mean value - Blank (STD A) | | 47381 | | 49441 | | 43744 | | 40921 |
| SD | 102 | 3620 | 43 | 3236 | 630 | 2259 | 76 | 3896 |
| CV % | 7.1 | 7.4 | 9.2 | 6.5 | 23.0 | 4.9 | 9.4 | 9.3 |

*The value has been excluded as an outlier

The significant decrease of background signal (over a three-fold decrease) is obvious from the results in Table 2. Surprisingly, also an increase of specific signal for compound 3 is observed. Moreover surprisingly, high increases in specific signal, even up to 40%, have been observed with different blocking reagents described in this application.

Compounds 3 and 8 were tested with several different tracer antibodies and assay concepts. The average performance for both compounds is presented in FIG. 9 together with the performance of other blocking compounds described in this application. In FIG. 9, the reference value represents the background signal for a standard assay with no additional background blocker. Values for compounds 6, 9 and 19 have been obtained by signal comparison to compound 8. Values for compounds 10-16 have been obtained by comparison to compound 6.

It is worth noticing that even when using strongly chelating ligands as blocking reagents, in high concentrations compared to the luminescent chelates used in the assay, it has no negative effect to the obtained specific signals.

As a whole, the background blocking principle of the present invention can be effectively applied by using individual chelates and ligands, chelates and ligands conjugated to antibodies, ligands conjugated to polymer, ligands conjugated to an organic molecule (hydrophobic group) and ligands conjugated to a hapten such biotin, and thus, ligands immobilized to a streptavidin coated surface.

The invention claimed is:

1. A binding assay for detecting at least one specific analyte in a sample, comprising:
   a) providing at least one first analyte-specific binding component immobilized onto a coated or uncoated solid support;
   b) adding to said solid support:
      1) at least one second analyte-specific binding component labelled with at least one first chelate comprising at least one first lanthanide ion selected from the group consisting of $Eu^{3+}$, $Tb^{3+}$, $Sm^{3+}$, and $Dy^{3+}$;
      2) a non-specific reagent, which is non-specific to said at least one analyte and to said at least one first analyte-specific binding component and to said at least one second analyte-specific binding component, which, in the presence of the at least one first analyte-specific binding component and the at least one second analyte-specific binding component, reduces non-specific background luminescence, and which is selected from the group consisting of:
         i) a biomolecule labelled with a second chelate, wherein said biomolecule is non-specific to said at least one analyte and to said at least one first analyte-specific binding component and to said at least one second analyte-specific binding components, and wherein the second chelate comprises at least one second lanthanide ion selected from the group consisting of $Gd^{3+}$, $La^{3+}$, $Lu^{3+}$, $Pr^{3+}$, $Nd^{3+}$, $Ho^{3+}$, $Er^{3+}$, and $Yb^{3+}$,
         ii) a biomolecule labelled with a first chelating ligand, wherein the biomolecule is non-specific to said at least one analyte and to said at least one first analyte-specific binding component and to said at least one second analyte-specific binding component,
         iii) a third chelate comprising at least one third lanthanide ion selected from the group consisting of $Gd^{3+}$, $La^{3+}$, $Lu^{3+}$, $Pr^{3+}$, $Nd^{3+}$, $Ho^{3+}$, $Er^{3+}$, and $Yb^{3+}$, and
         iv) a second chelating ligand,
      3) the sample; and
   c) detecting the at least one specific analyte by time-resolved fluorometry (TRF), wherein the at least one first chelate is a structure of Formula I:

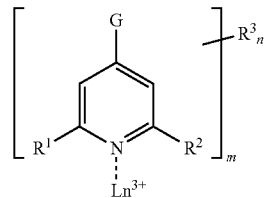

Formula I and the first chelating ligand, the second chelating ligand, the second chelate, and the third chelate is a structure of Formula I,
wherein each structure of Formula I comprises 1-5 pyridine moieties containing 1-5 of the same or different group(s) G, which are selected from the group consisting of a conjugating group, a single bond, and hydrogen;
and wherein
$Ln^{3+}$ represents the at least one first lanthanide ion of the at least one first chelate, the at least one second lanthanide ion of the second chelate, and the at least one third lanthanide ion of the third chelate, respectively, or is nothing in the case of the first chelating ligand and the second chelating ligand;
m is 1-5 and the dashed line represents a coordination bond between the pyridine nitrogen and $Ln^{3+}$, if present;
$R^1$ and $R^2$ represent i) additional chelating moieties Ch forming one or more coordination bond between the said heteroatoms and lanthanide, ii) a bond between the said pyridine moiety and other moieties of the compound, or iii) a bond between individual pyridine moieties of the formula (I);
each of $R^3{}_n$, in which n=1-5, is independently selected from the group consisting of a covalent group $Z^1$ formed from a reactive group $Z^2$ and a corresponding group in the biomolecule after coupling to the said biomolecule, a hydrophobic group, a hydrophilic group, and hydrogen.

2. The assay according to claim 1, wherein the at least one first and at least one second analyte-specific binding components are selected from the group consisting of a polyclonal antibody which may be genetically or chemically modified, a monoclonal antibody which may be genetically or chemically modified, an antigen, a protein, a peptide, a glycoprotein, a sugar, an oligosaccharide, a polysaccharide, a nucleotide sequence, a hapten, a lectin, an enzyme, a receptor, and an aptamer.

* * * * *

UNITED STATES PATENT AND TRADEMARK OFFICE
CERTIFICATE OF CORRECTION

| | |
|---|---|
| PATENT NO. | : 11,614,445 B2 |
| APPLICATION NO. | : 16/306997 |
| DATED | : March 28, 2023 |
| INVENTOR(S) | : Harri Takalo, Kaj Blomberg and Henri Sund |

It is certified that error appears in the above-identified patent and that said Letters Patent is hereby corrected as shown below:

In the Claims

Claim 1, Column 27, Lines 34-35, "one second analyte-specific binding components" should read --one second analyte-specific binding component--.

Signed and Sealed this
Eleventh Day of July, 2023

Katherine Kelly Vidal
*Director of the United States Patent and Trademark Office*